(12) United States Patent
Vlahov et al.

(10) Patent No.: US 7,910,594 B2
(45) Date of Patent: Mar. 22, 2011

(54) VITAMIN-MITOMYCIN CONJUGATES

(75) Inventors: Iontcho Radoslavov Vlahov, Lafayette, IN (US); Christopher P. Leamon, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 482 days.

(21) Appl. No.: 10/513,372

(22) PCT Filed: May 13, 2003

(86) PCT No.: PCT/US03/14969
§ 371 (c)(1),
(2), (4) Date: Nov. 3, 2004

(87) PCT Pub. No.: WO03/097647
PCT Pub. Date: Nov. 27, 2003

(65) Prior Publication Data
US 2005/0165227 A1    Jul. 28, 2005

Related U.S. Application Data

(60) Provisional application No. 60/380,579, filed on May 15, 2002, provisional application No. 60/425,918, filed on Nov. 13, 2002.

(51) Int. Cl.
| | | |
|---|---|---|
| A61K 31/40 | (2006.01) | |
| A61K 51/00 | (2006.01) | |
| A61P 35/00 | (2006.01) | |
| A61M 36/14 | (2006.01) | |
| C07D 487/14 | (2006.01) | |

(52) U.S. Cl. ....... 514/262.1; 514/18; 514/411; 544/261; 544/327; 548/308.7; 536/26.44; 424/1.73; 424/1.11; 424/1.85; 424/9.1

(58) Field of Classification Search .............. 548/22, 548/308.7; 514/12, 411, 18, 262.1; 544/327, 544/261; 536/26.44; 424/1.73, 1.11, 1.85, 424/9.1

See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 4,166,810 A | 9/1979 | Cullinan et al. |
| 4,203,898 A | 5/1980 | Cullinan et al. |
| 4,337,339 A | 6/1982 | Farina et al. |
| 4,691,024 A | 9/1987 | Shirahata et al. |
| 4,713,249 A | 12/1987 | Schroder |
| 4,801,688 A | 1/1989 | Laguzza et al. |
| 4,866,180 A | 9/1989 | Vyas et al. |
| 5,006,652 A | 4/1991 | Cullinan et al. |
| 5,094,849 A | 3/1992 | Cullinan et al. |
| 5,108,921 A | 4/1992 | Low et al. |
| 5,140,104 A | 8/1992 | Coughlin et al. |
| 5,266,333 A | 11/1993 | Cady et al. |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,291,673 B1 | 9/2001 | Fuchs et al. |
| 6,291,684 B1 | 9/2001 | Borzilleri et al. |
| 6,335,434 B1 | 1/2002 | Guzaev et al. |
| 6,365,179 B1 * | 4/2002 | Zalipsky et al. .............. 424/450 |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |

(Continued)

FOREIGN PATENT DOCUMENTS

CA        2372841        11/2000

(Continued)

OTHER PUBLICATIONS

Melby, Elisabeth L. et al; "Entry of Protein Toxins in Polarized Epithelial Cells"; Cancer Research, 53; Apr. 15, 1993, pp. 1755-1760.

(Continued)

*Primary Examiner* — Venkataraman Balasubramanian
(74) *Attorney, Agent, or Firm* — Barnes & Thornburg LLP

(57) ABSTRACT

This invention relates to vitamin-mitomycin conjugates, to a method of using the conjugates to selectively eliminate a population of pathogenic cells in a host animal harboring the pathogenic cells, and to a method of preparation of the conjugates. The conjugate is of the general formula

B-L-X wherein the group B is a vitamin, or an analog or a derivative thereof, that binds to a surface accessible vitamin receptor that is uniquely expressed, overexpressed, or preferentially expressed by a population of pathogenic cells, wherein the group L comprises a cleavable linker, and wherein the group X comprises a mitomycin compound, or an analog or a derivative thereof. An additional therapeutic agent, such as a chemotherapeutic agent, can be administered in combination with the conjugate.

19 Claims, 12 Drawing Sheets

U.S. PATENT DOCUMENTS

| | | | |
|---|---|---|---|
| 6,596,757 | B1 | 7/2003 | Chari et al. |
| 6,617,333 | B2 | 9/2003 | Rabindran et al. |
| 6,670,355 | B2 | 12/2003 | Azrulan et al. |
| 6,677,357 | B2 | 1/2004 | Zhu et al. |
| 6,680,330 | B2 | 1/2004 | Zhu et al. |
| 6,713,607 | B2 | 3/2004 | Caggiano et al. |
| 6,800,653 | B2 | 10/2004 | Regueiro-Ren et al. |
| 6,821,731 | B2 | 11/2004 | Gillis et al. |
| 6,915,855 | B2 | 7/2005 | Steele et al. |
| 6,958,153 | B1 | 10/2005 | Ormerod et al. |
| 7,019,014 | B2 | 3/2006 | Bernan et al. |
| 7,029,674 | B2 | 4/2006 | Carreno et al. |
| 7,060,709 | B2 | 6/2006 | Cooperstone et al. |
| 7,060,797 | B2 | 6/2006 | O'Toole et al. |
| 7,067,111 | B1 | 6/2006 | Yang et al. |
| 7,074,804 | B2 | 7/2006 | Zhu et al. |
| 7,105,328 | B2 | 9/2006 | Wood et al. |
| 7,122,361 | B2 | 10/2006 | Liu et al. |
| 7,128,893 | B2 | 10/2006 | Leamon et al. |
| 7,153,957 | B2 | 12/2006 | Chew et al. |
| 7,601,332 | B2 | 9/2009 | Vlahov et al. |
| 2001/0031252 | A1 | 10/2001 | Low et al. |
| 2003/0086900 | A1 | 5/2003 | Low et al. |
| 2003/0162234 | A1 | 8/2003 | Jallad |
| 2004/0018203 | A1 | 1/2004 | Pastan et al. |
| 2004/0033195 | A1 | 2/2004 | Leamon et al. |
| 2004/0242582 | A1 | 12/2004 | Green et al. |
| 2005/0002942 | A1 | 1/2005 | Vlahov et al. |
| 2005/0004010 | A1 | 1/2005 | Collins et al. |
| 2005/0026068 | A1 | 2/2005 | Gogolides et al. |
| 2005/0107325 | A1 | 5/2005 | Mancharan et al. |
| 2005/0165227 | A1 | 7/2005 | Vlahov et al. |
| 2005/0227985 | A9 | 10/2005 | Green et al. |
| 2005/0239713 | A1 | 10/2005 | Domling et al. |
| 2005/0239739 | A1 | 10/2005 | Matulic-Adamic et al. |
| 2006/0058266 | A1 | 3/2006 | Manoharan et al. |
| 2006/0128754 | A1 | 6/2006 | Hoefle et al. |
| 2007/0009434 | A1 | 1/2007 | Low et al. |
| 2007/0275904 | A1 | 11/2007 | Vite et al. |
| 2008/0056824 | A1 | 3/2008 | Blackwood |
| 2010/0004276 | A1 | 1/2010 | Vlahov et al. |
| 2010/0104626 | A1 | 4/2010 | Leamon et al. |

FOREIGN PATENT DOCUMENTS

| | | |
|---|---|---|
| CA | 2376175 | 12/2000 |
| EP | 0 116 208 A1 | 8/1984 |
| EP | 0116208 | 8/1984 |
| EP | 0 163 550 A2 | 12/1985 |
| EP | 0 247 792 | 12/1987 |
| EP | 0 354 728 | 2/1990 |
| EP | 0 280 741 A1 | 9/1998 |
| JP | 59-175493 | 10/1984 |
| JP | 60-255789 | 12/1985 |
| WO | WO 88/01622 | 3/1988 |
| WO | WO 9012096 | 10/1990 |
| WO | WO 91/07418 | 5/1991 |
| WO | WO96/36367 | 11/1996 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 0066091 | 11/2000 |
| WO | WO 00/74721 | 12/2000 |
| WO | WO 0128592 | 4/2001 |
| WO | WO 01/74382 | 10/2001 |
| WO | WO 02/085908 | 10/2002 |
| WO | WO 02/087424 | 11/2002 |
| WO | WO 02/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO 2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO 2005/112919 | 12/2005 |
| WO | WO 2006/012527 | 2/2006 |
| WO | WO 2006/042146 | 4/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | PCT/US2008/054189 | 2/2008 |
| WO | PCT/US2008/056824 | 3/2008 |
| WO | PCT/US2008068093 | 6/2008 |
| WO | WO 2009/002993 | 12/2008 |
| WO | WO 2009/055562 | 4/2009 |

OTHER PUBLICATIONS

Olsnes, Sjur et al; "Immunotoxins—entry into cells and mechanisms"; Immunology Today; vol. 10, No. 9, 1989, pp. 291-295.

DeVita, Jr., Vincent et al (eds); Biologic Therapy of Cancer; 2nd ed., J.B. Lippincott Company; 1995.

M. G. Nair, Otha C. Salter, Roy L. Kisliuk, Y. Gaumont, and G. North; "Folate Analogues. 22. Synthesis and Biological Evaluation of Two Analogues of Dihydrofolic Acid Processing a 7,8- Dihydro-8-oxapterin Ring System," journal article, J. Med. Chem., 1983, vol. 26, pp. 1164-1168.

Eugene C. Roberts and Y. Fulmer Shealy, "Folic Acid Analogs. Modifications in the Benzene-Ring Region. 3. Neohomofolic and Neobishomofolic Acids. An Improved Synthesis of Folic Acid and Its Analogs.", journal article, Journal of Medicinal Chemistry, 1973, vol. 16, No. 6, pp. 697-699.

Eugene C. Roberts and Y. Fulmer Shealy, "Folic Acid Analogs. Modifications in the Benzene-Ring Region. 2. Thiazole Analogs," journal article, Journal of Medicinal Chemistry, 1972, vol. 15, No. 12, pp. 1310-1312.

Eugene C. Roberts and Y. Fulmer Shealy, "Folic Acid Analogs. Modifications in the Benzene-Ring Region. 1. 2'- and 3'- Azafolic Acids," journal article, Journal of Medicinal Chemistry, 1971, vol. 14, No. 2, pp. 125-130.

Louis T. Weinstock, Bernard F. Grabowski, and C. C. Cheng, "Folic Acid Analogs. II. p-{[2,6-Diamino-8-purinyl)methyl]amino}—benzoyl-L-glutamic Acid and Related Compounds," journal article, Journal of Medicinal Chemistry, 1970, vol. 13, No. 5, pp. 995-997.

Lothar Bock, George H. Miller, Klaus-J. Schaper, and Joachim K. Seydel, "Sulfonamide Structure-Activity Relationships in a Cell-Free System. 2. Proof for the Formation of a Sulfonamide-Containing Folate Analog.," journal article, Journal of Medicinal Chemistry, 1974, vol. 17, No. 1, pp. 23-28.

Eugene C. Roberts and Y. Fulmer Shealy, "Folic Acid Analogs. Modifications in the Benzene-Ring Region. 4. 3'- Ethyl—and 3'-Isopropylfolic Acids," journal article, Journal of Medicinal Chemistry, 1974, vol. 17, No. 2, pp. 219-222.

William W. Lee, Abelardo P. Martinez, and Leon Goodman, "Folic Acid Antagonists. Methotrexate Analogs Containing Spurious Amino Acids. Dichlorohomofolic Acid.", journal article, Journal of Medicinal Chemistry, 1974, vol. 17, No. 3, pp. 326-330.

Y. H. Kim, Y. Gaumont, R. L. Kisliuk, and H. G. Mautner, "Synthesis and Biological Activity of 10-Thia-10-deaza Analogs of Folic Acid, Pteroic Acid, and Related Compounds," journal article, Journal of Medicinal Chemistry, 1975, vol. 18, No. 8, pp. 776-780.

M. G. Nair and Patricia T. Campbell, "Folate Analogues Altered in the C9-N10 Bridge Region. 10-Oxafolic Acid and 10-Oxaaminopterin," journal article, Journal of Medicinal Chemistry, 1976, vol. 19, No. 6, pp. 825-829.

Laurence T. Plante, Elizabeth J. Crawford, and Morris Friedkin; "Polyglutamyl and Polylysyl Derivatives of the Lysine Analogues of Folic Acid and Homofolic Acid," journal article, Journal of Medicinal Chemistry, 1976, vol. 19, No. 11, pp. 1295-1299.

John B. Hynes, Donald E. Eason, Claudia M. Garrett, and Perry L. Colvin, Jr., "Quinazolines as Inhibitors of Dihydrofolate Reductase. 4. Classical Analogues of Folic and Isofolic Acids," journal article, Journal of Medicinal Chemistry, 1977, vol. 20, No. 4, pp. 588-591.

John E. Oatis, Jr. and John B. Hynes, "Synthesis of Quinazoline Analogues of Folic Acid Modified at Position 10," journal article, Journal of Medicinal Chemistry, 1977, Vol. 20, No. 11, pp. 1393-1396.

M. G. Nair, P. Colleen O'Neal, C. M. Baugh, Roy L. Kisliuk, Y. Gaumont, and Michael Rodman; "Folate Analogues Altered in the C9-N10 Bridge Region: N10-Tosylisohomofolic Acid and N10-Tosylisohomoaminopterin," journal article, Journal of Medicinal Chemistry, 1978, vol. 21, No. 7, pp. 673-677.

M. G. Nair, Shiang-Yuan Chen, Roy L. Kisliuk, Y. Gaumont, and D. Strumpf; "Folate Analogues Altered in the C9-N10 Bridge Region: 11-Thiohomofolic Acid," journal article, Journal of Medicinal Chemistry, 1979, vol. 22, No. 7, pp. 850-855.

M. G. Nair, Colleen Saunders, Shiang-Yuan Chen, Roy L. Kisliuk, and Y. Gaumont; "Folate Analogues Altered in the C9-N10 Bridge Region. 14. 11-Oxahomofolic Acid, a Potential Antitumor Agent," journal article, J. Med. Chem., 1980, vol. 23, pp. 59-65.

M. G. Nair, Timothy W. Bridges, Timothy J. Henkel, Roy L. Kisliuk, Y. Gaumont, and F. M. Sirotnak; "Folate Analogues Altered in the C9-N10 Bridge Region. 18. Synthesis and Antitumor Evaluation of 11-Oxahomoaminopterin and Related Compounds," journal article, J. Med. Chem., 1981, vol. 24, pp. 1068-1073.

Carroll Temple, Jr., L. Lee Bennett, Jr., Jerry D. Rose, Robert D. Elliott, John A. Montgomery, and John H. Mangum; "Synthesis of Pseudo Cofactor Analogues as Potential Inhibitors of the Folate Enzymes," journal article, J. Med. Chem., 1982, vol. 25, pp. 161-166.

M. G. Nair, Eldrige B. Otis, Roy L. Kisliuk, and Y. Gaumont, "Folate Analogues. 20. Synthesis and Antifolate Activity of 1, 2, 3, 4, 5, 6,—Hexahydrohomofolic Acid," journal article, J. Med. Chem., 1983, vol. 26, pp. 135-140.

M. G. Nair, David C. Salter, R. L. Kisliuk, Y. Gaumont, G. North, and F. M. Sirotnak; "Folate Analogues. 21. Synthesis and Antifolate and Antitumor Activities of N10-(Cyanomethyl)-5,8-dideazafolic Acid," journal article, J. Med. Chem., 1983, vol. 26, pp. 605-607.

U.S. Appl. No. 10/765,336, filed Jan. 27, 2004, Vlahov et al.

U.S. Appl. No. 11/632,895, filed Jan. 19, 2007, Vlahov et al.

U.S. Appl. No. 11/908,695, filed Sep. 13, 2007, Xu et al.

U.S. Appl. No. 12/064,163, filed Feb. 19, 2008, Leamon et al.

U.S. Appl. No. 12/064,191, filed Feb. 19, 2008, Vlahov et al.

Verwey, J., "Mitomycin C-Induced Renal Toxicity, a Dose-Dependent Side Effect?", Eur J Cancer Clin Onco, vol. 23, No. 2, 1987, pp. 195-199.

E.S. Agoston, M. A. Hatcher, T. W. Kensler, G. H. Posner; "Vitamin D Analogs as Anti-Carcinogenic Agents," journal article, Anti-Cancer Agents in Medicinal Chemistry, 2006, pp. 53-71.

Anderson et al., "Potocytosis: Sequestration and transport of small molecules by caveolae," Science 255: 410-411 (1992).

Antony, "The biological chemistry of folate receptors," Blood, vol. 79, No. 11, pp. 2807-2820 (1992).

Antony, "Folate receptors," Annu Rev Nutr, vol. 16, pp. 501-21 (1996).

Antony, et al. "Studies of the Role of a Particulate Folate-Binding Protein in the Uptake of 5-Methyltetrahydrofolate by Cultured Human KB Cells," Journal of Biological Chemistry, vol. 260, No. 28, 1985, pp. 14911-14917.

Archer, et al. "Separation of Folic Acid Derivatives and Pterins by High-Performance Liquid Chromatography," Methods in Enzymology, vol. 66, 1980 p. 452.

Arya et al., "Design and Synthesis of Analogs of Vitamin E: Antiproliferative Activity Against Human Breast Adenocarcinoma Cells," Bioorganic & Medicinal Chemistry Letters, vol. 8, 1998, p. 2433.

Ayers, "Effect of Vitamin B12 and Analogs on the Respiration of a Marine Bacterium," journal article, Archives of Biochemistry and Biophysics, vol. 96, pp. 210-215 (1962).

Barnett et al., "Structure-Activity Relationships of Dimeric Catharanthus Alkaloids. 1. Deacetylvinblastine Amide (Vindesine) Sulfate," J. Med. Chem., vol. 21, pp. 88-96 (1978).

Birinberg E. M. et al., "Synthesis and antimetabolic activity of pyrimidine analogs of folic and pteroic acids," Pharmaceutical Chemistry Journal, 1969; 3(6): pp. 331-333.

Boger et al., "An Improved Synthesis of 1,2,9,9a-Tetrahydrocyclopropa[c]benz[e]indol-4-one (CBI): A Simplified Analogue of the CC-1065 Alkylation Subunit," J. Org. Chem., vol. 57, pp. 2873-2876 (1992).

Boothe, et al, "Pteroic Acid Derivatives. II. Pteroyl-γ-glutamylglutamic Acid and Pteroyl-γ-glutamyl-α-glutamylglutamic Acid," Pteroic Acid Derivatives, vol. 70, 1948, pp. 1099-1102.

Campbell et al., "Folate-binding protein is a marker for ovarian cancer," Cancer Res., vol. 51, pp. 5329-5338 (1991).

Cho et al., "Single-chain Fv/folate conjugates mediate efficient lysis of folate-receptor-positive tumor cells," Bioconjug. Chem., vol. 8, No. 3, pp. 338-346 (1997).

Christensen et al., "Membrane receptors for endocytosis in the renal proximal tubule," Int. Rev. Cytol., 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," Organomettalics, 1999; 18(21): 4270-4274.

Citro G. et al., "Inhibition of leukemia cell proliferation by folic acid - polylysine-mediated introduction of c-myb antisense oligodeoxynucelotides into HL-60 cells," Br. J. Cancer, 1994; 69: 463-467.

Cope et al. "Thermal Rearrangement of Allyl-type Sulfoxides, Sulfones and Sulfinates," Thermal Rearrangement of Allyl-Type Sulfoxides, SUlfones and Sulfinates, vol. 72, 1950, pp. 59-67.

D. B. Cosulich, J. M. Smith Jr., "Analogs of Pteroylglutamic Acid. I. N10-Alkylpteroic Acid and Derivatives," JACS, 1948, 70 (5), pp. 1922-1926.

Shealy Y.F., "Synthesis and Evaluation of Some New Retinoids for Cancer Chemoprevention," Preventive Medicine, 1989, vol. 18, pp. 624-645.

Domling et al., "Myxobacterial Epothilones and Tubulysins as Promising Anticancer Agents," Molecular Diversity, 2005, vol. 9, pp. 141-147.

Douglas et al., "Targeted Gene Delivery by Tropisum-Modified Adenoviral Vectros," Nat. Biotechnol., vol. 14, pp. 1574-1578 (1996).

Eichman, J.D. et al., "The Use of PAMAM Dendrimers In The Efficient Transfer Of Genetic Material Into Cells" Jul. 2000 PSTT vol. 3, No. 7, pp. 232-245.

Foong, L.Y. et al., "Development of a Novel Thiol Reagent for Probing Ion Channel Structure: Studies in a Model System," Biochemistry, 1997, vol. 36, pp. 1343-1348.

Frankel AE., "Immunotoxin therapy of cancer," Oncology, 1993; 7(5): 69-78.

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," J Med Chem., 2008; 51(15):4589-4600.

Garin-Chesa et al., "Trophoblast and ovarian cancer antigen LK26. Sensitivity and specificity in immunopathology and molecular identification as a folate-binding protein," Am. J. Pathol. 142(2): 557-562 (1993).

GE Healthcare, Instructions 71-7104-00 AD. ion exchange, Sephadex, 16 pages.

Gottschalk S. et al., "Folate receptor mediated DNA delivery into tumor cells: potosomal disruption results in enhanced gene expression," Gene Therapy, 1994; 1(3): 185-191.

Hanck A.B. et al., "Dexpanthenol (Ro 01-4709) in the treatment of constipation," Acta Vitaminol Enzymol, 1982; vol. 4 (1-2), pp. 87-97 (abstract only).

Harvison, P.J. et al., "Synthesis and Biological. Activity of Novel Folic Acid Analogues: Pteroyl-S-alkylhomocysteine Sulfoximines," Journal of Medicinal Chemistry, 1992, vol. 35, pp: 1227-1233.

Ho R. I. et al., "A simple radioassay for dihydrofolate synthetase activity in Escherichia coli and its application to an inhibition study of new pteroate analogs," Anal. Biochem., 1976, 73(2), pp. 493-500.

Hofland et al., "Folate-targeted gene transfer in vivo," Mol Ther 5(6): 739-744 (2002).

Hofle, G. et al., "Semisynthesis and Degradation of the Tubulin Inhibitors Epothilone and Tubulysin", 2003, Pure Appl. Chem., vol. 75, Nos. 2-3, pp. 167-178.

Holladay et al., "Riboflavin-mediated delivery of a macromolecule into cultured human cells," Biochim Biophys Acta, 1426(1): 195-204 (1999).

Holm, J. et al., "Folate receptors in malignant and benign tissues of human female genital tract," *BioSci. Rep.*, 17(4): 415-427 (1997).

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Akihiro Hosomi, et al. "Affinity for a-tocopherol transfer protein as a determinant of the biological activities of vitamen E analogs," journal article, Federation of European Biochemical Societies, 1997, vol. 409, pp. 105-108.

Houlihan, C. M. et al., "Preparation and Purification of Pteroic Acid from Folic Acid," *Analytical Biochemistry*, 1972, vol. 46, pp. 1-6.

Jones T.R. et al., "A potent antitumour quinazoline inhibitor of thymidylate synthetase: synthesis, biological properties and therapeutic results in mice," *Eur J Cancer*, 1981; 17(1):11-9.

Jones T.R. et al., "Quinazoline antifolates inhibiting thymidylate synthase: variation of the amino acid," *J Med Chem*, 1986; 29(6):1114-8.

Jung K.H. et al., "Intramolecular o-glycoside bond formation," *Chem. Rev.*, 2000, 100, 4423-42.

Kagechika, Hiroyuki et al., "Synthetic Retinoids: Recent Developments Concerning Structure And Clinical Utility," Journal Article, Journal Of Medicinal Chemistry, Sep. 22, 2005, vol. 48, No. 19, pp. 5875-5883.

Kamao, Maya et al., "Determination Of Plasma Vitamin K By High Performance Liquid Chromatography With Fluorescence Detection Using Vitamin K Analogs As Internal Standards," Journal Article, Journal of Chromatography B, vol. 816, 2005, pp. 41-48.

Kamen et al., "Delivery of folates to the cytoplasm of MA104 cells is mediated by a surface receptor that recycles," J. Biol. Chem., vol. 263, pp. 13602-13609 (1988).

Kamen et al. "Receptor-mediated folate accumulation is regulated by the cellular folate content," Proc. Natl. Acad. Sci. USA, vol. 83, pp. 5983-5987 (1986).

Kamen et al., "The folate receptor works in tandem with a probenecid-sensitive carrier in MA104 cells in vitro," J. Clin. Invest., vol. 87, No. 4, pp. 1442-1449 (1991).

Kandiko et al., "Inhibition of Rat Brain Pyruvate Dehydrogenase by Thiamine Analogs," journal article, Biochemical Pharmacology, vol. 37, No. 22, pp. 4375-4380 (1988).

Kane et al., "The influence of extracellular folate concentration on methotrexate uptake by human KB cells. Partial characterization of a membrane-associated methotrexate binding protein," *J. Biol. Chem.* 261: 44-49 (1986).

Kranz et al., "Conjugates of folate and anti-T-cell-receptor antibodies specifically target folate-receptor-positive tumor cells for lysis," *Proc. Natl. Acad. Sci. USA* 92(20), 9057-9061 1995.

Kumar et al. "Folate Transport in *lactobacillus salivarius*," Journal fo Biological Chemistry, 1987, vol. 262, No. 15, pp. 7171-7179.

Ladino et al., "Folate-maytansinoids: target-selective drugs of low molecular weight," *Int. J. Cancer* 73(6): 859 864 (1997).

J. P. Lambooy, "Riboflavin Analogs Utilized for Metabolism by a Lactobacillus Casei Mutant," Int. J. Biochem., vol. 16, No. 2, 1984, pp. 231-234.

Landuer, Walter et al., "The Interaction In Teratogenic Activity Of The Two Niacin Analogs 3-Acetylpyridine And 6-Aminonicotinamide," Storrs Agricultural Experiment Station, University Of Connecticut, Undated, pp. 253-258.

Langone et al., "radioimmunoassay for the vinca alkaloids, vinblastine and vincristine," analytical biochemistry, vol. 95, 1978, pp. 214-221.

Leamon et al., "comparative preclinical activity of the folate-targeted vinca alkaloid conjugates EC140 and EC145," Int. J. Cancer. vol. 121, 2007, pp. 1585-1592.

Leamon et al, "Cytotoxicity of folate-Pseudomonas exotoxin conjugates toward tumor cells. Contribution of translocation domain," J. Biol. Chem., vol. 268, No. 33, pp. 24847-24854 (1993).

Leamon et al., "Cytotoxicity of momordin-folate conjugates in cultured human cells," J. Biol. Chem., vol. 267, No. 35, pp. 24966-24971 (1992).

Leamon et al., "Delivery of macromolecules into living cells: a method that exploits folate receptor endocytosis," Proc. Natl. Acad. Sci. USA, vol. 88, No. 13, pp. 5572-5573 (1991).

Leamon et al., "Synthesis and Biological Evaluation of EC20: A New Folate-Derived, (99m)Tc-Based Radiopharmaceutical," Bioconjug. Chem., vol. 13, No. 6, pp. 1200-1210 (2002).

Leamon et al., "Folate-mediated drug delivery: effect of alternative conjugation chemistry," J. Drug Target, vol. 7, No. 3, pp. 157-169 (1999).

Leamon, C. P. and Low, P. S., "Folate-mediated targeting: from diagnostics to drug and gene delivery," *Drug Discovery Today* 6: 36-43 (2001).

Leamon et al., "Folate Targeted Chemotherapy," Advanced drug delivery reviews, vol. 56, 2004, pp. 1127-1141.

Leamon et al., "Membrane folate-binding proteins are responsible for folate-protein conjugate endocytosis into cultured cells," Biochem. J., vol. 291, pp. 855-860 (1993).

Leamon et al., "Selective targeting of malignant cells with cytotoxin-folate conjugates," J. Drug Target, vol. 2, No. 2, pp. 101-112 (1994).

Leamon et al., "synthesis and biological evaluation of EC72: a new folate targeted chemotherapeutic," Bioconjuages Chem. vol. 16, 2005, pp. 803-811.

Leamon et al., "synthesis and biological evaluation of EC140: a new folate targeted vinca alkaloid conjugate," Chem. vol. 17, 2006, pp. 1226-1232.

Lee et al, "Measurement of Endosome pH Following Folate Receptor-Mediated Endocytosis," *Biochim. Biophys. Acta* 1312(3): 237-242 (1996).

Lee et al., "Synthesis and evaluation of taxol-folic acid conjugates as targeted antineoplastics," *Bioorg Med Chem.* 10(7): 2397-2414, (2002).

Lee, Francis Y. F., et al., "BMS-247550: A Novel Epothilone Analog With A Mode Of Action Similar To Paclitaxel But Possessing Superior Antitumor Efficacy," *Clin Cancer Res*, 2001, No. 7, pp. 1429-1437.

Lee, R. J. and Huang, L., "Folate-Targeted, Anionic Liposome-Entrapped Polylysine-Condensed Dna For Tumor Cell-Specific Gene Transfer," *J. Biol. Chem.* 271(14): 8481-8487 (1996).

Lee R. J. and Low, P. S, "Delivery of liposomes into cultured KB cells via folate receptor-mediated endocytosis," *J. Biol. Chem.* 269(5): 3198-3204 (1994).

Lemon, et al. "Conversion of pteroylglutamic acid to pteroic acid by bacterial degradation," Archives of biochemistry, vol. 19, 1998, pp. 311-316.

Levy, et al., "The enzymatic hydrolysis of methotrexate and folic acid," journal of biological chemistry, vol. 242, No. 12, 1967, pp. 2933-2938.

Lewis et al., "Receptor-mediated folate uptake is positively regulated by disruption of actin cytoskeleton," Cancer Res., vol. 58, No. 14, pp. 2952-2956 (1998).

Li et al "Targeted delivery of antisense oligodeoxynucleotides by LPDII," J. Liposome Res., vol. 7, No. 1, pp. 63-75 (1997).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).

Lonsdale, Derrick "A Review Of The Biochemistry, Metabolism And Clinical Benefits Of Thiamin(E) And Its Derivatives," Publication, Advance Access Publication, vol. 3, Feb. 2006, pp. 49-59, 1988.

Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low, "folate receptor-targeted drugs for cancer and inflammatory diseases," advanced drug delivery reviews, vol. 56, 2004, pp. 1055-1058.

Lu et al., "Folate-mediated delivery of macromolecular anticancer therapeutic agents," Adv. Drug Del Rev. vol. 54, No. 5, pp. 675-693 (2002).

Lu et al., "Folate-targeted enzyme prodrug cancer therapy utilizing penicillin-V amidase and a doxorubicin prodrug," J. Drug Target, vol. 7, No. 1, pp. 43-53 (1999).

Lu et al., "Folate targeting of haptens to cancer cell surfaces mediates immunotherapy of syngeneic murine tumors," Cancer Immunol Immunother., vol. 51, pp. 153-162 (2002).

Luo et al., "Efficient syntheses of pyrofolic acid and pteroyl azide, reagents for the production of carboxyl-differentiated derivatives of folic acid," J. Am. Chem. Soc., vol. 119, pp. 10004-10013 (1997).
Mack et al., "The Carboxylation Activity of Vitamin K Analogs with Substitutions at Position 2, 3, or 5," The Journal of Biological Chemistry, vol. 254, pp. 2656-2664 (1979).
Mancuso et al., "Activated dimethyl sulfoxide: useful reagents for synthesis," Reviews, 1981, pp. 165-185.
March, advanced organic chemistry, 1992, John Wiley and Sons, 4th ed. pp. 362-363, 816, 885, 896.
Mathias, C. J. and Green, M. A., "A kit formulation for preparation of [(111)In]In-DTPA-folate, a folate-receptor-targeted radiopharmaceutical," Nucl. Med. Biol. 25(6): 585-587 (1998).
Mathias et al., "Indium- 111-DTPA-Folate as a potential folate-receptor-targeted radiopharmaceutical," J. Nucl. Med. 39(9): 1579-1585 (1998).
Mathais et al., "Receptor-mediated targeting of 67Ga-deferoxamine-folate to folate-receptor-positive human KB tumor xenografts," Nucl Med Biol, 26(1): 23-25 (1999).
Mathias CJ, Hubers D, Low PS, Green MA. Synthesis of [(99m)Tc]DTPA-folate and its evaluation as a folate-receptor-targeted radiopharmaceutical. Bioconjug Chem. 2000; 11(2):253-257.
Mathias et al., "Tumor-Selective Radiopharmaceutical Targeting Via Receptor-Mediated Endocytosis of Gallium-67-Deferoxamine-Folate," J. Nucl. Med., vol. 37, No. 6, pp. 1003-1008 (1996).
Matsui et al., "Studies on mitomycins. 3. The synthesis and properties of mitomycin derivatives," J Antibio, vol. 21, pp. 189-198 (1968).
McAlinden, et al., "Synthesis and biological evaluation of a fluorescent analogue of folic acid," biochemistry, vol. 30, 1991, pp. 5674-5681.
McHugh et al., "demonstration of a high affinity folate binder in human cell membranes and its characterization in cultured human KB cells," journal fo biological chemistry, vol. 254, No. 22, 1979, pp. 11312-11318.
Melani et al., "Targeting of interleukin 2 to human ovarian carcinoma by fusion with a single-chain Fv of antifolate receptor antibody," Cancer Res., vol. 58, No. 18, pp. 4146-4154 (1998).
Mislick et al., "Transfection of folate-polylysine DNA complexes: evidence for lysosomal delivery," Bioconjug. Chem., vol. 6, No. 5, pp. 512-515 (1995).
Mock et al., "Urinary Biotin Analogs Increase in Humans During Chronic Supplementation: the Analogs are Biotin Metabolites," The American Physiological Society, pp. 83-85 (1997).
Morshed et al., "Folate transport proteins mediate the bidirectional transport of 5-methyltetrahydrofolate in cultured human proximal tubule cells," J. Nutr. 127(6): 1137-1147 (1997).
Neuss, N. et al., "Vinca Alkaloids. XXX (1). Chemistry Of The Deoxyvinblastines (Deoxy-VLB), Leurosine (VLR), And Pleurosine, Dimeric Alkaloids From Vinca," Tetrahedron Letters, No. 7, pp. 783-787 (1968).
J. Neuzil, K. Kagedal, L. Andrea, C. Weber, and U.T. Brunk, "Vitamin E Analogs: A New Class of Multiple Action Agents with Anti-Neoplastic and Anti-Atherogenic Activity," Apoptosis, vol. 7, 2002, pp. 179-187.
Nielsen, Peter et al., "Phosphates of Riboflavin And Riboflavin Analogs: A Reinvestigation By High-Performance Liquid Chromatography," Journal Article, Analytical Biochemistry, vol. 130, 1983, pp. 359-368.
R. H. Nimmo-Smirth, D.J. Brown, "Some Effects of 2-deaminopteroylglutamic Acid upon Bacterial Growth," J. Gen. Microbial. 1953, 9, pp. 536-544.
Nishikawa, Y. et al., "Growth Inhibition of Hepatoma Cells Induced by Vitamin K and Its Analogs." Journal of Biochemistry 1995, vol. 270, No. 47, Nov. 24, pp. 28304-28310.
Nomura, Makoto et al., "Development of an Efficient Intermediate a-[2-(Trimethylsily1)ethoxy]-2-N-[2-(trimethylsily1)ethoxycarbony1]folic Acid, for the Synthesis of Folate (γ)-Conjugates, and Its Application to the Synthesis of Folate-Nucleoside Conjugates," Journal Of Organic Chemistry, 2000, vol. 65, pp. 5016-5021.
Nosaka K.et al., "Separate Determination of Anticoccidial Thiamine Analogs by High-performance Liquid Chromatography," ActaA Vitaminol. Et Enzymol, 1984, vol. 6 (2), pp. 137-142.

Patrick et al., "Folate Receptors As Potential Therapeutic Targets in Choroid Plexus Tumors of Sv40 Transgenic Mice," J. Neurooncol. 32(2): 111-123 (1997).
Patrick et al., "Intracerebral bispecific ligand-antibody conjugate increases survival of animals bearing endogenously arising brain tumors," Int. J. Cancer 78(4): 470-79 (1998).
Peltier, et al., "The total synthesis of tubulysin D," j. Am. Chem. Soc, vol. 128, 2006, pp. 16018-16019.
G. Pizzorno, J. A. Sokoloski, A. R. Cashmore, B. A. Moroson, A. D. Cross, G.P. Beardsley, "Intracellular metabolism of 5,10-dideazatetrahydrofolic acid in human leukemia cell lines," Molecular Pharmacology, 1991, 39 (1), pp. 85-89.
Politis, I. et al., "The Effect of Various Vitamin E Derivatives on the Urokinase-Plasmogen Activator System of Ovine Macrophages and Neutrophils." British Journal of Nutrition, 2003, vol. 89, pp. 259-265.
Prabhu et al., "Arabidopsis dihydropteroate synthase: general properties and inhibition by reaction product and sulfnoamides," phytochemistry. vol. 45, No. 1. 1997, pp. 23-27.
Prasad et al., "Functional coupling between a bafilomycin A1-sensitive proton pump and a probenecid-sensitive folate transporter in human placental choriocarcinoma cells," Biochim. Biophys. Acta, vol. 1222, No. 2, pp. 309-314 (1994).
Pratt, et al., "Thy hydrolysis of mono-, di-, and trigultamate derivates of folic acid with bacterial enzymes," Journal of biological chemistry, vol. 243, No. 24, 1968, pp. 6367-6372.
Punj et al., "Effect of Vitamin D Analog (1 α Hydroxy D5) Immunoconjugates to Her-2 Antibody on Breast Cancer," Int. J. Cancer, vol. 108, pp. 922-929 (2004).
Raghavan et al., "Cytotoxic simplified tubulysin analogues," J. Med. Chem. vol. 51, 2008 pp. 1530-1533.
Ranasinghe, et al., "Facile synthesis of unsymmetrical thiolsulfonates via sulfonylation of mercaptans," Communications, vol. 18, No. 3, 1998, pp. 227-232.
Reddy et al., "Folate-Mediated Targeting of Therapeutic and Imaging Agents to Cancers," Crit. Rev. The. Drug Carrier Syst., vol. 15, No. 6, pp. 587-627 (1998).
Reddy et al., "Optimization of folate-conjugated liposomal vectors for folate receptor-mediated gene therapy," J. Pharm. Sci 88(11): 1112-1118 (1999).
Reddy, "preclinical evaluation of EC145, a folate-vinca alkaloid conjugate," Cancer res. vol. 676, No. 9, 2007, pp. 4434.
Reddy, retargeting of viral vectors to the folate receptor endocytic pathway, journal of controlled release, vol. 74, 2001, pp. 77-82.
Renz et al., "Synthesis of 4-Aza-5, 6-diethylbenzimidazole and Biosynthetic Preparation of 4- and 7-Aza-5, 6-dimethylbenzimidazolylcobamide," journal article, Z. Naturforsch, vol. 52c, pp. 287-291 (1997).
Rijnboutt et al., "Endocytosis of GPI-linked membrane folate receptor-alpha," J. Cell Biol. 132(1-2): 35-47 (1996).
Rose, W.C., "Taxol-based combination chemotherapy and toerh in vivo preclinical antitumor studies," journal of national cancer institute monographs, No. 15, 1993, pp. 47-53.
Ross et al., "Differential regulation of folate receptor isoforms in normal and malignant tissues in vivo and in established cell lines. Physiologic and clinical implications," Cancer, vol. 73, No. 9, pp. 2432-2443 (1994).
Rothberg et al, "Cholesterol controls the clustering of the glycophospholipid-anchored membrane receptor for 5-methyltetrahydrofolate," J. Cell Biol., vol. 111, No. 6, pp. 2931-2938 (1990).
Rothberg et al., "The glycophospholipid-linked folate receptor internalizes folate without entering the clathrin-coated pit endocytic pathway," J. Cell Biol., vol. 110, No. 3, pp. 637-649 (1990).
Roy et al., "Targeting T cells against brain tumors with a bispecific ligand-antibody conjugate," Int. J. Cancer, vol. 76, No. 5, pp. 761-66 (1998).
Sadasivan et al., "The complete amino acid sequence of a human folate binding protein from KB cells determined from the cDNA," J. Biol. Chem., 1989; 264: 5806-5811.
Sargent D.R. et al., "Antimetabolites of Pantothenic Acid, Ureido - and Carbamoyl-Derivatives," Texas Reports on Biology and Medicine, 1975, vol. 33, No. 3, pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-1α,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969: 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits Plasmodium Falciparum Pantothenate Kinase and Repress the Proliferation of Malaria Parasites," *Antimicrobial Agents and Chemotherapy*, 2005; 49(11), 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.
Toffoli et al., "Overexpression of folate binding protein in ovarian cancers," *Int. J. Cancer* 74(2): 193-198 (1997).
Toraya T. et al., "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh A. et al., "Temperature-sensitive differential affinity of TRAIL for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006;16(19), 5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci USA* 92(8), 3318-3322, (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.
Wiener et al., "Targeting dendrimer-chelates to tumors and tumor cells expressing the high-affinity folate receptor," *Invest. Radial.* 32(12): 748-54 (1997).
Wu M. et al., "Clustering of GPI-anchored folate receptor independent of both cross-linking and association with caveolin," *J. Membr. Biol.* 159(2): 137-147 (1997).
Zimmer H. et al., "Potential anticancer agents V., Synthesis of folic acid and pteroic acid analogs derived of caffeine and theophylline," *Arzneimittelforschung*, 1966, 16(4), pp. 541-545.
Zimmerman, J., "Folic acid transport in organ-cultured mucosa of human intestine. Evidence for distinct carriers," *Gastroenterol.* 99(4): 964-972 (1990).
Greene T.E. et al., "Protective Groups ion Organic Synthesis," 2d edition, John Wiley & Sons, Inc. New York (1991).
Larock R.C., "Comprehensive Organic Transformations, a guide to functional group preparations," VCH Publishers, Inc. New York (1989).
Lee, R. J. and Low, P. S., "Folate-mediated tumor cell targeting of liposome-entrapped doxorubicin in vitro," *Biochim. Biophys. Acta* 1233: 134-144 (1995).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

Remington: The Science & Practice of Pharmacy, 21th Edition (Lippincott Williams & Wilkins, 2005).

Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.

Bavetsias, V., et al., "The design and synthesis of water-soluble analogues of CB30865, a quinazolin-4-one-based antitumor agent," J Med Chem, 2002; 45(17): 3692-3702.

Gibbs, DD et al., "BGC 945, a novel tumor-selective thymidylate synthase inhibitor targeted to alpha-folate receptor-overexpressing tumors," Cancer Res, 2005; 65(24): 11721-11728.

Henderson, E.A. et al., Targeting the alpha-folate receptor with cyclopenta[g]quinazoline-based inhibitors of thymidylate synthase, Bioorg Med Chem, 2006; 14(14): 5020-5042.

Jackman, A. L. et al., "Antifolates targeted specifically to the folate receptor," Adv Drug Deliv Rev, 2004; 56(8): 1111-1125.

Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).

Wikipedia, Derivative (Chemistry), http://en.wikipedia.org/wiki/Derivative_(chemistry), downloaded Dec. 16, 2009.

U.S. Appl. No. 12/739,579, filed Apr. 23, 2010, Vlahov et al.

U.S. Appl. No. 12/775,824, filed May 7, 2010, Green et al.

Wikipedia, Analog (Chemistry), http://en.wikipedia.org/wiki/Analog_(chemistry), downloaded Dec. 16, 2009.

Wikipedia, List of Purification Methods in Chemistry, http://en.wikipedia.org/wiki/List_of purification_methods_in_chemistry, downloaded Dec. 16, 2009.

Wikipedia, Solution, http://en.wikipedia.org/wiki/Solution, downloaded Dec. 17, 2009.

Principles of Ion Exchange Chromatography, http://www.separations.us.tosohbioscience.com/ServiceSupport/TechSupport/ResourceCenter/PrinciplesofChromatography/ IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid Its Derivatives" *J. Org. Chem.* 2000;65:1562-1565.

U.S. Appl. No. 12/666,712, filed Dec. 24, 2009, Leamon et al.

Carl et al. "A novel connector linkage applicable in prodrug design" J. Med. Chem. 1981;24(5):479-480.

Coney et al. "Cloning of a tumor-associated antigen: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Chemistry: A Guide To Successful Synthesis Design," Wiley-VCII, Weinheim, 2005, p. ix of preface.

Forgac. "Structure and function of vacuolar class of ATP-driven pumps" Physiological Rev. 1989; 69(3) :765-795.

Garrett et al. "Synthesis and characterisation of polyamine-poly(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance"in Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Kamen et al., 1986, "Receptor-mediated folate accumulation is regulated by cellular folate content" Proc. Natl. Acad. Sci., U.S.A. 83, 5983-5987.

Ke et al. "Targeting the Tumor-Associated Folate Receptor with a 111 IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

U.S. Appl. No. 60/590,580, filed Jul. 23, 2004, Vlahov et al.

Kemp et al. "New Protective Groups for Peptide Synthesis-I The Bic Group Base and Solvent Lability of the 5 -B enzi soxazolymethyl eneoxycarbonyl amino function" Tet. Lett. 1975;52:4625-4628.

Kutsky RJ. Handbook of Vitamins, Minerals, and Hormones, 2 Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Linder et al., "In vitro & in vivo studies with a-and y-isomers of 99"Tc-oxa folate show uptake of both isomers in folate receptor (+) KB Cell Lines J. Nuclear Med. 2000;41(5):470 Suppl.

Mchvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor—Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. Invest. 1971; 50(3):719-726.

Selhub et al. "The folate binding protein of rat kidney. Purification, properties, and cellular distribution" J. Biol. Chem. 1984;259(10):6601-6606.

Selhub et al. "Renal folate adsorption and the kidney folate binding protein I. Urinary Clearance studies" Am. J Physiol. 252:F750-F756.

Selhub et al. "Renal folate adsorption and the kidney folate binding protein II. Microinfusion studies" Am. J. Physiol. 252:F757-F760.

Sirotnak. "Obligate genetic expression in tumor cells of a fetal membrane property mediating "Folate" transport: biological significance and implications for improved therapy of human cancer" Cancer Res., 1985;45(9):3992-4000.

Stein et al. "Normal tissue reactivity of four anti-tumor monoclonal antibodies of clinical interest" Int. J. Cancer 1991;47(2):163-169.

Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.

Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.

Toffoli et al. "Expression of folate binding protein as a prognostic factor for response to platinum-containing chemotherapy and survival in human ovarian cancer" Int. J. Cancer (Pred. Oncol) 1998; 79:121-126.

Weitman et al. "Distribution of the folate receptor GP38 in normal and malignant cell lines and tissues" Cancer Res. 1992;52(12):3396-3401.

Westerhof et al. "Membrane transport of natural folates and antifolate compounds in murine L1210 Leukemia cells: role of carrier-and receptor mediated transport systems" Cancer Res. 1991;51:5507-5513.

Williams et al. "Renal tubular transport of folic acid and methotrexate in the monkey" Am. J. Physiol 1982; 242(5):F484-490.

Weygand, et al., Chemishe. Berichte (1950) 83, 460-467.

International Search Report for PCT/US2003/014969, dated Sep. 16, 2003.

Beevers, Christopher S., et al., "Curcumin Inhibits the Mammalian Target of Rapamycin-Mediated Signaling Pathways in Cancer Cells", 2006; Int. Journal Cancer; Vo. 119; pp. 757-764.

Brown, Nicole E., et al., "Delayed Cystogenesis and Increased Ciliogenesis Associated with th Re-Expression of Polaris in Tg737 Mutant Mice", 2003, Kidney International, vol. 63, pp. 1220-1229.

Bukanov Nikolay, O. et al., "Long-Lasting Arrest Of Murine Polycystic Kidney Disease With CDK Inhibitor Roscovitine", Dec. 14, 2006; Nature; vol. 444; pp. 949-952.

Hay, Nissim, et al., "Upstream and Downstream of mTOR", 2004, Genes & Development, vol. 18, No. 16, pp. 1926-1945.

Kennedy, Michael D., et al., "Evaluation of Folate Conjugate Uptake and Transport by the Choroid Plexus of Mice", (May 2003), vol. 20, No. 5, pp: 714-719.

Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.

Nauta, Jeroen, et al., "Renal and Biliary Abnormalities in a New Murine Model of Autosomal Recessive Polycystic Kidney Disease", 1993, Pediatr. Nephrol. No. 7, pp. 163-172.

Piontek, Klaus B., et al. "A Functional Floxed Allele of Pkd1 that Can Be Conditionally Inactivated In Vivo", J. Am. Soc. Nephrol. vol. 15, pp. 3035-3043.

Shillingford, Jonathan M., et al., "The mTOR Pathway is Regulated by Polycystin-1, and its Inhibition Reverses Renal Cystogenesis in Polycyclic Kidney Disease", Apr. 4, 2006, PNAS. vol. 103, No. 14, pp. 5466-5471.

Ke CY et al., "Folate-Receptor-Targeting of In-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Antony, "Folate receptors: reflections on a personal odysssey and a perspective on unfolding truth," Advanced Drug Delivery Reviews, 2004; vol. 56: 1059-66.

Lu et al., "Folate receptor-targeted immunotherapy of cancer: mechanism and therapeutic potential," Advanced Drug Delivery Reviews, 2004; vol. 56: 1161-76.

Roy et al., "Folate-mediated targeting of T cells to tumors," Advanced Drug Delivery Reviews, 2004; vol. 56: 1219-31.

Angier, R. B., et al., "Pteroic Acid Analogs Containing Arsenic," J. American Chem. Soc., vol. 76, 1954, pp. 902-904.

Ke et al., "Folate-receptor-targeted radionuclide imaging agents," Advanced Drug Delivery Reviews, 2004; vol. 56: 1143-60.

Gabizon et al., "Tumor cell targeting of liposome-entrapped drugs with phospholipid-anchored folic acid-PEG Conjugates," Advanced Drug Delivery Reviews, 2004; vol. 56: 1177-92.

Zhao et al., "Tumor-selective targeted delivery of genes and antisense oligodeoxyribonucleotides via the folate receptor," Advanced Drug Delivery Reviews, 2004; vol. 56: 1193-1204.

Pantos CM et al., "Ligand Binding and Kinetics of Folate Receptor Recycling in Vivo: Impact on Receptor-Mediated Drug Delivery," Molecular Pharmacology, 2004; 66:1406-1414.

Griesser UJ, "The Importance of Solvents," in Polymorphism in the Pharmaceutical Industry, Hilfiker ed., 2006; p. 211-230.

Wikipedia, Structural analog, http://en.wikipedia.org/wiki/Structural_analog, downloaded Apr. 7, 2009.

Wikipedia, Functional analog, http://en.wikipedia.org/wiki/Functional_analog, downloaded Apr. 7, 2009.

Wikipedia, Folic acid, http://en.wikipedia.org/wiki/Folic_acid, downloaded Apr. 7, 2009.

Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.

* cited by examiner

VITAMIN-MITOMYCIN CONJUGATES

CROSS-REFERENCE TO RELATED APPLICATIONS

This application is a U.S. national counterpart application of international application serial no. PCT/US03/14969 filed May 13, 2003, which claims the benefit of U.S. provisional application Ser. Nos. 60/380,579 and 60/425,918 filed May 15, 2002, and Nov. 13, 2002, respectively.

FIELD OF THE INVENTION

This invention relates to compositions and methods for use in treating disease states characterized by the proliferation of pathogenic cell populations. More particularly, the invention relates to vitamin-mitomycin conjugates, to a method of using the conjugates to selectively eliminate a population of pathogenic cells in a host animal, and to a method of preparation of the conjugates.

BACKGROUND OF THE INVENTION

The mammalian immune system provides a means for the recognition and elimination of tumor cells, other pathogenic cells, and invading foreign pathogens. While the immune system normally provides a strong line of defense, there are many instances where cancer cells, other pathogenic cells, or infectious agents evade a host immune response and proliferate or persist with concomitant host pathogenicity. Chemotherapeutic agents and radiation therapies have been developed to eliminate replicating neoplasms. However, most, if not all, of the currently available chemotherapeutic agents and radiation therapy regimens have adverse side effects because they work not only to destroy cancer cells, but they also affect normal host cells, such as cells of the hematopoietic system. The adverse side effects of the currently available anticancer drugs highlight the need for the development of new therapies specific for pathogenic cell populations and with reduced host toxicity.

Researchers have developed therapeutic protocols for destroying cancer cells by targeting cytotoxic compounds to such cells. Many of these protocols utilize toxins conjugated to antibodies that bind to antigens unique to or overexpressed by cancer cells in an attempt to minimize delivery of the toxin to normal cells. Using this approach certain immunotoxins have been developed consisting of antibodies directed to specific antigens on pathogenic cells, the antibodies being linked to toxins such as ricin, Pseudomonas exotoxin, Diptheria toxin, and tumor necrosis factor. These immunotoxins target tumor cells bearing the specific antigens recognized by the antibody (Olsnes, S., Immunol. Today, 10, pp. 291-295, 1989; Melby, E. L., Cancer Res., 53(8), pp. 1755-1760, 1993; Better, M. D., PCT Publication Number WO 91/07418, published May 30, 1991). Although the immunotoxins are directed to specific antigens on pathogenic cells, the toxin component of these compounds may exhibit toxicity to normal host cells. The use of vitamins to deliver chemotherapeutic agents to cells has also been described (see U.S. Pat. No. 5,416,016).

Another approach for targeting populations of cancer cells or foreign pathogens in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the tumor cell surface to display the constant region of the antibodies on the cell surface and thereby induce tumor cell killing by various immune-system mediated processes (DeVita, V. T., Biologic Therapy of Cancer, 2d ed. Philadelphia, Lippincott, 1995; Soulillou, J. P., U.S. Pat. No. 5,672,486). However, these approaches have been complicated by the difficulties in defining tumor-specific antigens. Thus, there remains a significant need for effective therapies with minimized host toxicity directed to the treatment of disease states characterized by the existence of pathogenic cell populations in the affected host.

Mitomycins are natural products known to exhibit antitumor activity. Mitomycins can be produced by fermentation of Streptomyces caespitosus, and representive known mitomycins include mitomycin A, mitomycin B, mitomycin C, mitomycin D, mitomycin E, mitomycin F, and porfiromycin. The structures of these compounds are depicted by the following generic formula with substituents as shown in Table 1.

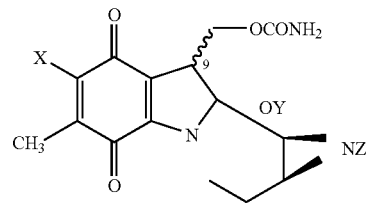

TABLE 1

| Mitomycin | X | Y | Z | C-9 |
|---|---|---|---|---|
| A | $OCH_3$ | $CH_3$ | H | β |
| B | $OCH_3$ | H | $CH_3$ | α |
| C | $NH_2$ | $CH_3$ | H | β |
| D | $NH_2$ | H | $CH_3$ | α |
| E | $NH_2$ | $CH_3$ | $CH_3$ | α |
| F | $OCH_3$ | $CH_3$ | $CH_3$ | β |
| J | $OCH_3$ | $CH_3$ | $CH_3$ | α |
| Porfiromycin | $NH_2$ | $CH_3$ | $CH_3$ | β |

Mitomycins are a class of cytotoxic drugs known as quinone-containing alkylating agents. Reduction of the quinone moiety results in the formation of bi-functional alkylating species that can form covalent bonds with a variety of cellular components including DNA. The interaction with DNA results in the formation of DNA crosslinks leading to the induction of apoptosis and cell death, and this interaction is thought to be the most important contributor to the antitumor activity of mitomycin compounds.

SUMMARY OF THE INVENTION

The present invention relates to conjugates comprising a vitamin moiety linked to a mitomycin compound by a cleavable linker, to their use in the treatment of disease states characterized by the proliferation of a pathogenic cell population, and to a method of preparation of the conjugates. The vitamin-mitomycin conjugates in accordance with the invention can be used to selectively eliminate a population of pathogenic cells in an affected host. The selective elimination of the pathogenic cells is mediated by the binding of the vitamin moiety of the vitamin-mitomycin conjugate to a vitamin receptor, transporter, or other surface-presented protein that specifically binds the targeting vitamin, and which is uniquely expressed, overexpressed, or preferentially expressed by the pathogenic cells. The vitamin-mitomycin conjugates can be internalized into the targeted cells upon binding of the vitamin moiety to such a receptor, transporter, or surface-expressed protein, and, with the presence of a cleavable linker used to conjugate the vitamin moiety to the mitomycin compound, the vitamin moiety and the mitomycin compound can dissociate intracellularly. The dissociated mitomycin compound thereafter interacts with DNA, such as by forming crosslinks with DNA, resulting in killing or inhibition of proliferation of the pathogenic cells.

Surface-expressed vitamin receptors, such as the high-affinity folate receptor, are overexpressed, for example, on cancer cells. Epithelial cancers of the ovary, mammary gland, colon, lung, nose, throat, and brain have all been reported to express elevated levels of the folate receptor. In fact, greater than 90% of all human ovarian tumors are known to express large amounts of this receptor. Accordingly, the present invention can be used for killing or inhibiting the proliferation of a variety of tumor cell types, and of other types of pathogenic cells that overexpress vitamin receptors.

Although mitomycins are known to exhibit excellent anti-tumor activity, mitomycins also exhibit cytotoxicity towards leukocytes in the host animal treated with these compounds. In an effort to increase the anti-tumor activity of mitomycins and/or to decrease the undesired toxicity of these compounds, derivatives of mitomycins have been prepared which contain a variety of modifications at the C-7-amino group in the aminomitosane skeleton. Among the known mitomycin derivatives with reduced toxicity are unsymmetrical dialkyl disulfides containing C-7 substituents of the formula RSS(CH$_2$)$_2$NH— in which i) R is an alkyl group (see European Patent Application No. 0116208A1 and Japanese Patent Application No. 175493/84), ii) R contains an aromatic ring (see European Patent Application Nos. 0116208A1 and 0163550A2, Japanese Patent Application No. 255789/85, and U.S. Pat. No. 4,866,180), and iii) R is structurally related to amino acid or peptide fragments (see European Patent Application No. 0163550A2, Japanese Patent Application No. 255789/85, and U.S. Pat. No. 4,691,024).

All known methods for the preparation of such unsymmetrical dialkyl disulfides are based on a transthiolation of unsymmetrical heteroaryl-alkyl disulfides with alkyl thiol. Notably, the most common heteroarylthio leaving groups are 2-thiopyridyl (see WO 88/01622 and European App. Publication No. 0116208A1) and 3-nitro-2-thiopyridine (see U.S. Pat. No. 4,691,024). The driving force for this cleavage reaction is the excellent leaving group properties of the heteroarylthio moiety. The reaction is as follows:

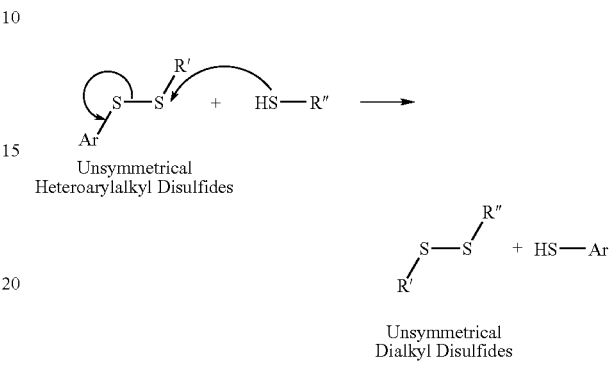

Unsymmetrical Heteroarylalkyl Disulfides

Unsymmetrical Dialkyl Disulfides

The vitamin-mitomycin conjugates in accordance with the present invention can be prepared using such transthiolation methods or, for example, by a novel process for the preparation of unsymmetrical dialkyl disulfides that is based on the thiophilicity of thiosulfonate reagents. The synthetic scheme for the preparation of the thiosulfonate reagents, mitomycin A, and for the synthesis of a vitamin derivative (e.g., cysteine-terminated folate) for use in this preparation process is shown in scheme 1 below (Fmoc=9-fluorenylmethyloxycarbonyl; Boc=tert-butyloxycarbonyl; Dap=diaminopropionic acid; DMF=dimethylformamide; DIPEA=diisopropylethylamine; DMSO=dimethylsulfoxide; TFAA=trifluoroacetic acid; PyBOP=benzotriazole-1-yl-oxy-tris-(pyrrolidinophosphoniumhexafluoro-phosphate)).

SCHEME 1

Synthesis of Thiolsulfonates[a]:

R = Alkyl or Aryl
Examples: Alkyl = CH$_3$
Aryl = p—CH$_3$—C$_6$H$_4$- a) M.G. Ranasinghe, P.L. Fuchs, *Synthetic Communications*, 18(3)m 277-232 (1988)

Synthesis of Mitomycin A[b]:

Mitomycin C

-continued

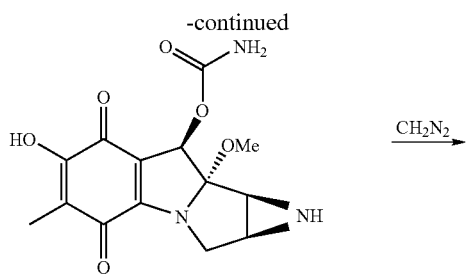

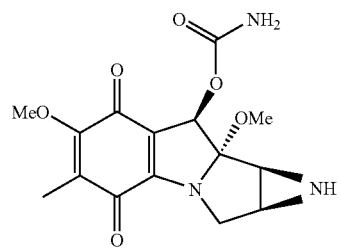

Mitomycin A (2)

b) M. Matsui, Y. Yamada, K. Uzu, T. Hirata, *J. Antibiot*, 21, 189-198 (1968); D. Vias, D. Benigni, R. Partyka, T. Doyle, J. Org. Chem. 51, 4307-4309 (1986).

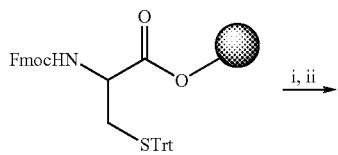

SCHEME 1

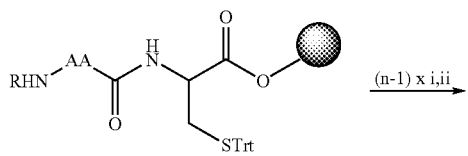

i ⌐ R = Fmoc
  └► R = H

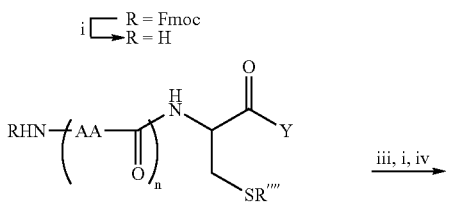

i ⌐ R = Fmoc
  └► R = H

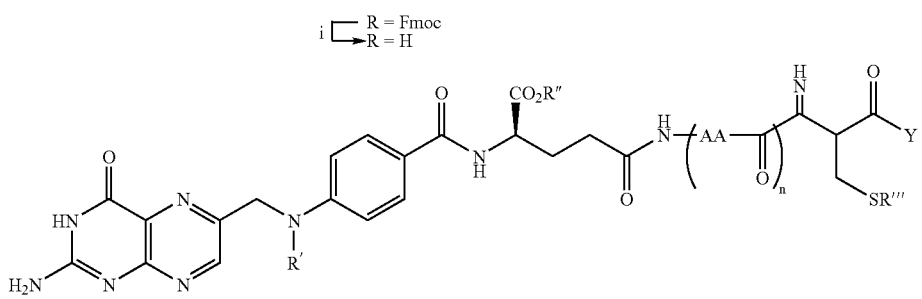

v  ⌐ R' = F₃CCO, R'' = tBu, R''' = Boc, R'''' = Trt, Y = Wang Resin
vi ├► R' = F₃CCO, R'' = H, R''' = H, R'''' = H, Y = OH
   └► R' = H, R'' = H, R''' = R'''' = H, Y = OH AA = Any Amino Acid Reagents and conditions: *i*) 20% Piperidine, DMF; *ii*) Fmoc-AA-OH, PyBop, DIPEA, DMF; *iii*) Fmoc-D-Glu-OtBu, PyBop, DIPEA, DMF; *iv*) $N^{10}$-TFA-Pte-OH, DIPEA, DMSO; *v*) TFAA, HSCH₂CH₂SH, iPr₃SiH; *vi*) H₄NOH, pH = 10.3

Examples:

4 (n = 0)

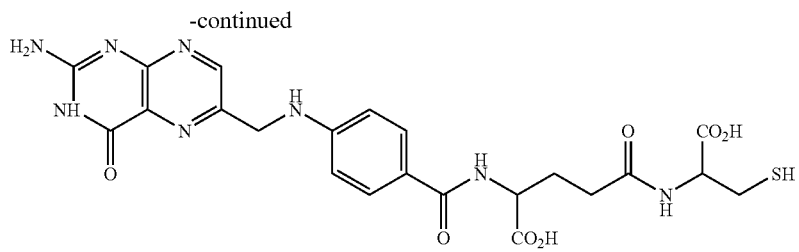

6 (n = 3)

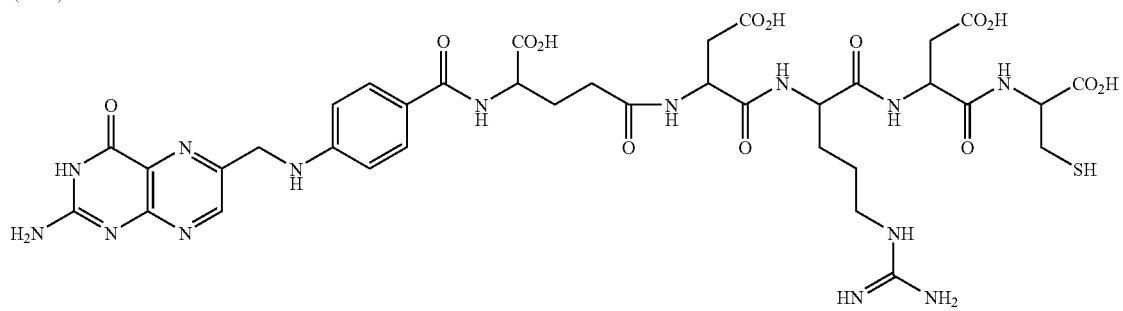

Exemplary synthetic schemes for the synthesis of the present vitamin-mitomycin conjugates as unsymmetrical dialkylsulfides using thiosulfonates are presented as schemes 2 and 3 below. In the disulfide-linked conjugates, one of the alkyl moieties is attached to the C-7-amino group in the mitosane skeleton, and the other is covalently attached via a divalent linker or directly to a vitamin molecule, or a vitamin receptor binding analog or derivative thereof.

SCHEME 2

Synthesis of Unsymmetrical Dialkylsulfides Using Thiolsulfonates

1)

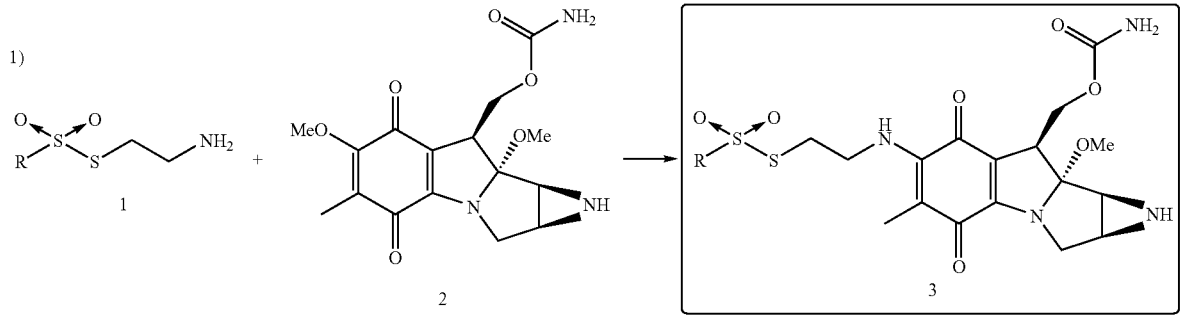

R = Alkyl or Aryl
Examples: Alkyl = CH₃
Aryl = p-CH₃-C₃H₄-

2)

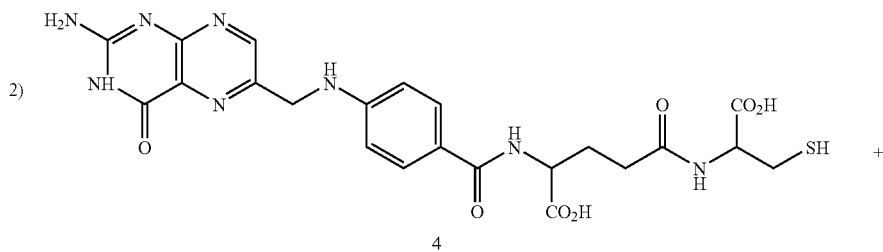

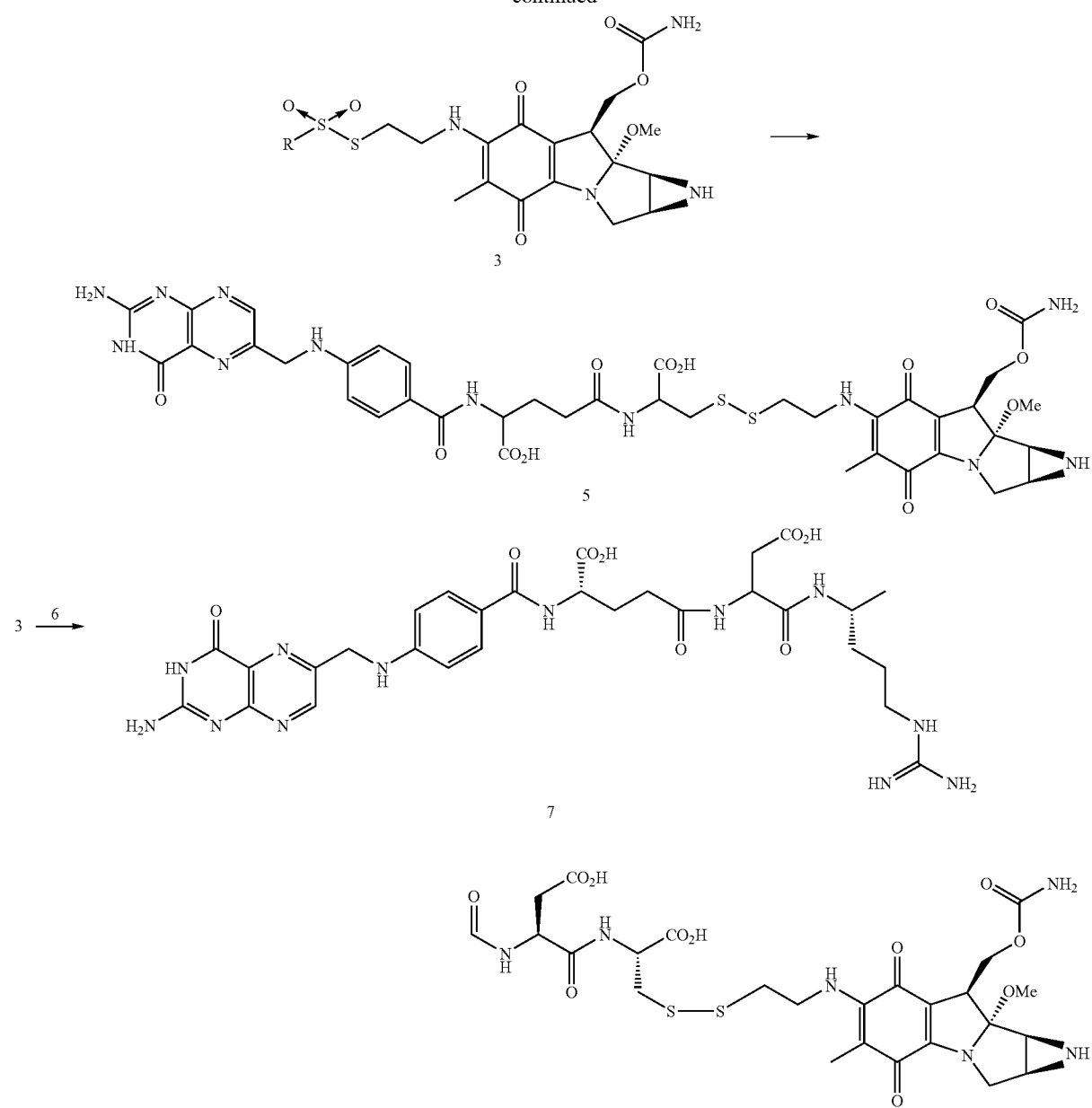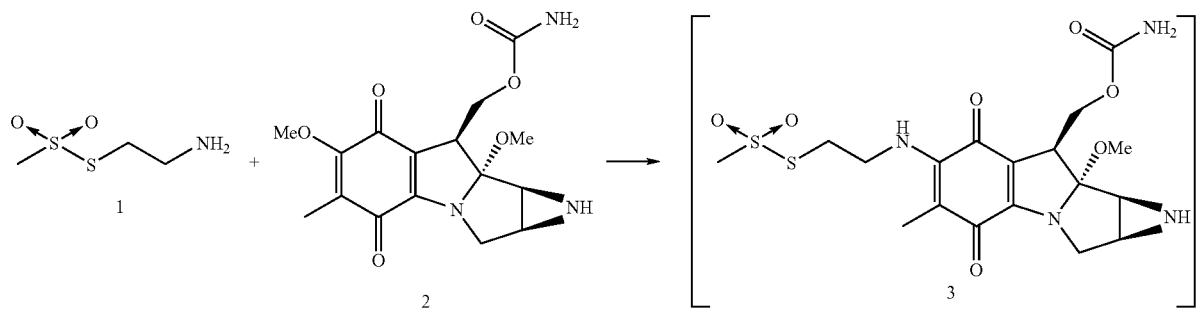

-continued

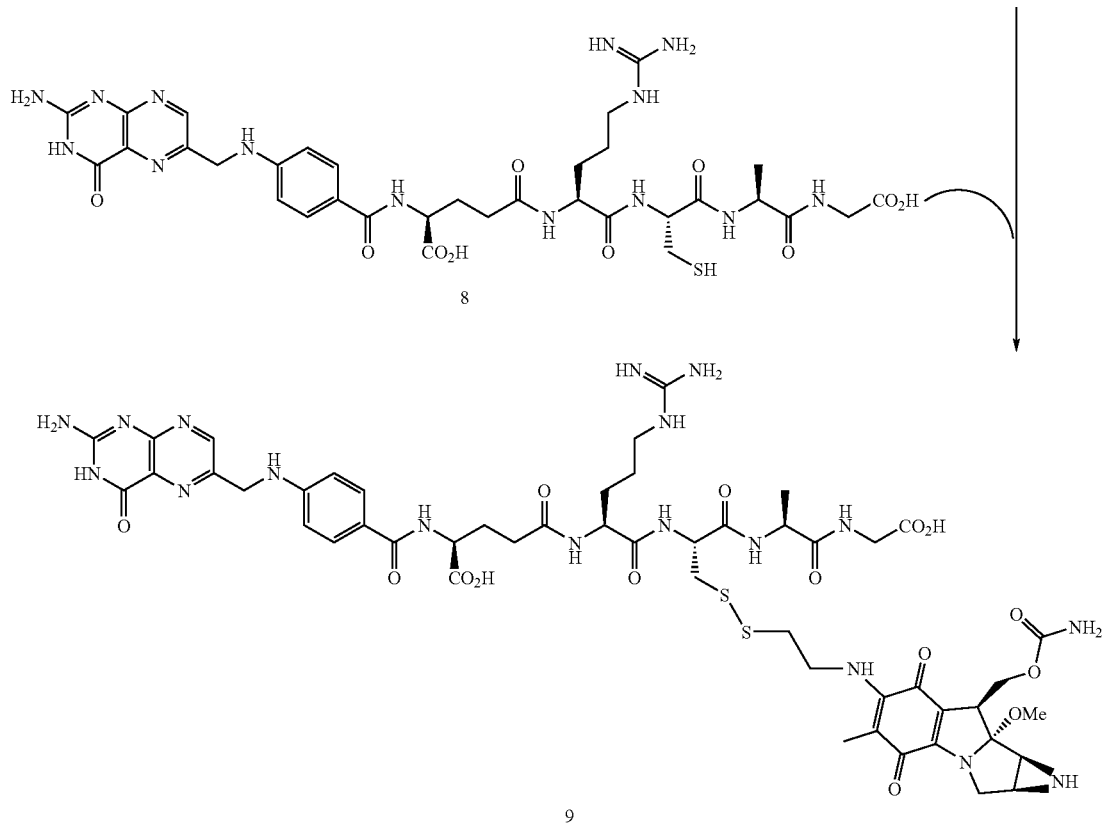

8

9

In both schemes 2 and 3, a commercially available amine 1, containing a thiolsulfonate group, was first reacted with the vinylogous methyl ester at C-7 in the quinone moiety of the mitosane derivative 2. Second, the resulting thiolsulfonate reagent 3 is used for sulfonylation of thiols, such as that found on pteroyl-glutamyl-cysteine 4, on Pte-Glu-Asp-Arg-Asp-Cys-OH 6, or Pte-Glu-Arg-Cys-Ala-Gly-OH 8, which are all folic acid derivatives. The instantaneous disulfide formation produces a vitamin-mitomycin conjugate, for example, a pteroyl-Glu-Cys-S-mitomycin C conjugate 5, a Pte-Glu-Asp-Arg-Asp-Cys-S-mitomycin C—OH conjugate 7, or a Pte-Glu-Arg-Cys-S-mitomycin C-Ala-Gly-O conjugate 9, in almost quantitative yield.

In embodiments of the present invention where the disulfide linkage is an unsymmetrical dialkyl disulfide, such as an unsymmetrical dialkyl disulfide prepared by the above-described procedure, the vitamin-mitomycin conjugates selectively eliminate the pathogenic cells, and have reduced toxicity towards normal cells. In embodiments where the vitamin moiety is conjugated to a mitomycin compound by such a disulfide linkage, the vitamin moiety and mitomycin compound can dissociate under the reducing conditions that exist intracellularly.

In one embodiment is provided a conjugate of the general formula

B-L-X wherein the group B is a vitamin, or an analog or a derivative thereof, that binds to a surface accessible vitamin receptor that is uniquely expressed, overexpressed, or preferentially expressed by a population of pathogenic cells, wherein the group L comprises a cleavable linker, and wherein the group X comprises a mitomycin compound or an analog or a derivative thereof.

In another embodiment is provided a method of selectively eliminating a population of pathogenic cells in a host animal harboring the population of cells wherein the members of the cell population have a surface accessible binding site for a vitamin. The method comprises the steps of administering to the host a conjugate of the general formula

B-L-X wherein the group B is a vitamin, or an analog or a derivative thereof, that binds to a surface accessible vitamin receptor that is uniquely expressed, overexpressed, or preferentially expressed by the population of pathogenic cells, wherein the group L comprises a cleavable linker, and wherein the group X comprises a mitomycin compound or an analog or a derivative thereof, and selectively eliminating the population of pathogenic cells.

In an alternate embodiment, the method can further comprise the step of administering to the host animal a chemotherapeutic agent such as paclitaxel.

In yet another embodiment is provided a pharmaceutical composition comprising a conjugate of the general formula

B-L-X wherein the group B is a vitamin, or an analog or a derivative thereof, that binds to a surface accessible vitamin receptor that is uniquely expressed, overexpressed, or preferentially expressed by a population of pathogenic cells, wherein the group L comprises a cleavable linker, and wherein the group X comprises a mitomycin compound or an analog or a derivative thereof, and a pharmaceutically acceptable carrier therefor.

In another embodiment, the pharmaceutical composition can further comprise a chemotherapeutic agent such as paclitaxel.

In still another embodiment is provided a method of preparing a biologically active conjugate of the formula

B-L-X wherein B is a vitamin or a vitamin-receptor-binding analog or derivative thereof;

X comprises a mitomycin compound or an analog or derivative thereof;

and L is a divalent linker comprising a disulfide bond, the method comprising the steps of forming a thiosulfonate intermediate of the formula B-(L')$_n$SSO$_2$R or an intermediate of the formula X-(L')$_n$SSO$_2$R and reacting the thiosulfonate intermediate with a compound of the formula X-(L')$_n$-SH or B-(L")$_n$-SH, respectively, wherein L' and L" are, independently, divalent linkers through which the thiol group SH is covalently bonded to B and X, respectively;

n and n' are 1 or 0; and

R is alkyl, substituted alkyl, aryl, heteroaryl or substituted aryl or heteroaryl.

DETAILED DESCRIPTION OF THE INVENTION

Figure 1:
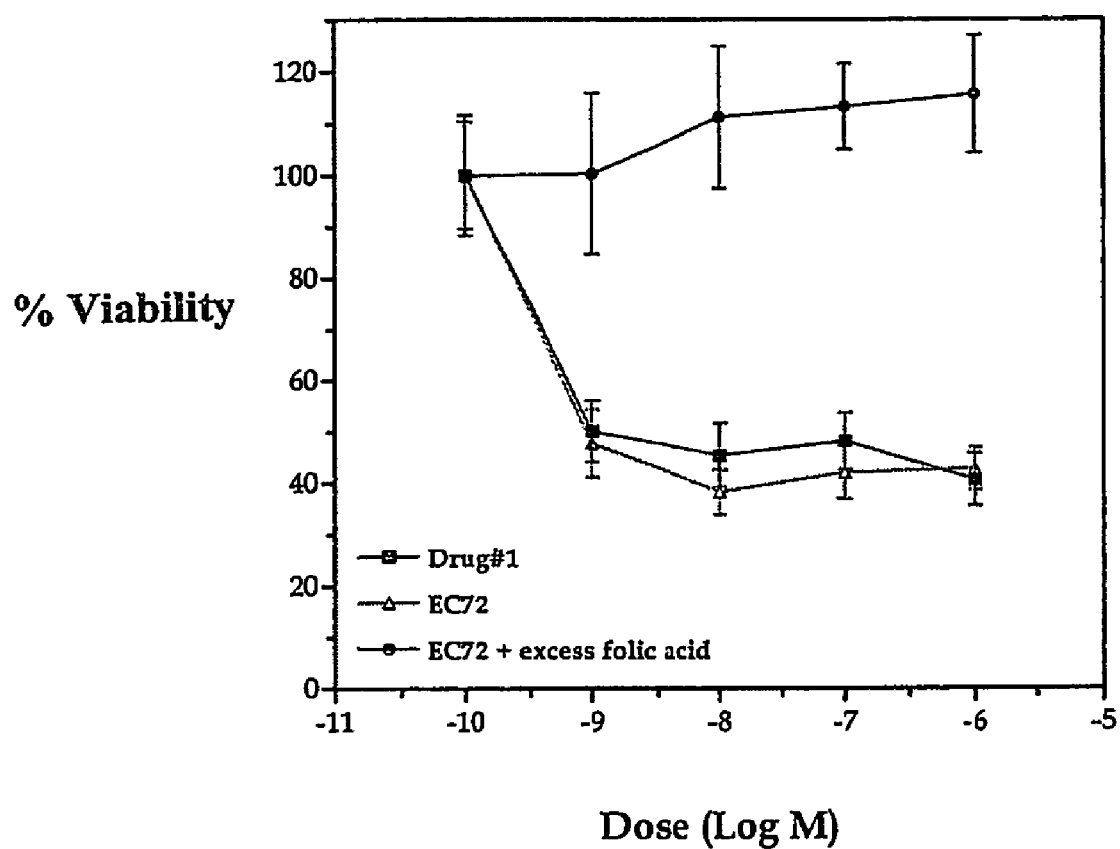
FIG. 1 shows a comparison between the cytotoxicities of EC72 (see scheme 1; closed triangles) and mitomycin C (closed squares). The cytotoxicity of EC72 in the presence of excess free folate (closed circles) is also shown.

The present invention relates to conjugates comprising a vitamin moiety linked to a mitomycin compound by a cleavable linker. The vitamin-mitomycin conjugates in accordance with the invention can be used to selectively eliminate a population of pathogenic cells in an affected host. The selective elimination of the pathogenic cells is mediated by the binding of the vitamin moiety of the vitamin-mitomycin conjugate to a vitamin receptor, transporter, or other surface-presented protein that specifically binds vitamins or vitamin analogs and which is uniquely expressed, overexpressed, or preferentially expressed by the pathogenic cells. A surface-presented protein uniquely expressed, overexpressed, or preferentially expressed by the pathogenic cells is preferably a receptor not present or present at lower concentrations on non-pathogenic cells providing a means for selective elimination of the pathogenic cells.

The vitamin-mitomycin conjugates are internalized upon binding of the vitamin moiety to such a receptor, transporter, or surface-expressed protein and the vitamin moiety and the mitomycin compound can dissociate intracellularly upon cleavage of a cleavable linker used to covalently link the vitamin moiety to the mitomycin compound. The cleavable linker can be, for example, a disulfide linkage which results in reduced toxicity of the vitamin-mitomycin conjugate towards normal cells. In embodiments where the vitamin moiety is conjugated to a mitomycin compound by a disulfide linkage, the vitamin moiety and mitomycin compound can dissociate under the reducing conditions that exist intracellularly. Upon its dissociation from the vitamin moiety, the mitomycin compound can interact with DNA, such as by forming crosslinks with DNA, resulting in killing or inhibiting the proliferation of the pathogenic cells.

In an alternative embodiment, the vitamin moiety of the conjugate can bind to the pathogenic cell placing the mitomycin compound in close association with the cell surface. The drug can then be released by cleavage of the disulfide linkage, for example, by a protein disulfide isomerase. The mitomycin compound can be taken up by the pathogenic cell to which the vitamin-mitomycin conjugate is bound, or the mitomycin compound can be taken up by another pathogenic cell in close proximity thereto to interact with the cell's DNA and kill or inhibit proliferation of the pathogenic cell. Alternatively, the drug could be released by a protein disulfide isomerase inside the cell where the releasable linker is a disulfide group.

In another embodiment, or in combination with the above-described embodiments, the vitamin-mitomycin conjugates can act through a mechanism independent of cellular vitamin receptors. For example, the conjugates can bind to soluble vitamin receptors present in the serum or to serum proteins, such as albumin, resulting in prolonged circulation of the conjugates relative to unconjugated mitomycin, and in increased activity of the conjugates towards the pathogenic cell population relative to unconjugated mitomycin.

The vitamin-mitomycin conjugates in accordance with the invention are utilized to selectively eliminate a population of pathogenic cells in a host animal harboring the population of pathogenic cells. The invention is applicable to populations of pathogenic cells that cause a variety of pathologies including cancer, diseases mediated by activated macrophages, and diseases mediated by any other type of pathogenic cells that overexpress vitamin receptors or receptors that bind analogs or derivatives of vitamins. Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The invention can be utilized to treat such cancers as carcinomas, sarcomas, lymphomas, Hodgekin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of conjugate administration is a therapeutic response measured by reduction or elimination of tumor mass, maintenance of tumor mass, or of inhibition of tumor cell proliferation. In the case of a tumor, the elimination can be an elimination of cells of the primary tumor or of cells that have metastasized or are in the process of dissociating from the primary tumor. A prophylactic treatment with the vitamin-mitomycin conjugate to prevent return of a tumor after its removal by any therapeutic approach including surgical removal of the tumor, radiation therapy, chemotherapy, or biological therapy is also contemplated in accordance with this invention. The prophylactic treatment can be an initial treatment with the vitamin-mitomycin conjugate, such as treatment in a multiple dose daily regimen, and/or can be an additional treatment or series of treatments after an interval of days or months following the initial treatments(s). Accordingly, elimination of the pathogenic cell population includes elimination of cells, inhibition of proliferation of pathogenic cells, maintenance of tumor mass, or a prophylactic treatment that prevents return of pathogenic cells.

The method of the present invention can be used for both human clinical medicine and veterinary applications. Thus, the host animal harboring the population of pathogenic cells and treated with vitamin-mitomycin conjugates can be human or, in the case of veterinary applications, can be a laboratory, agricultural, domestic, or wild animal. The present invention can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In accordance with the present invention, the vitamin-mitomycin conjugates can be formed from a wide variety of vitamins or receptor-binding vitamin analogs/derivatives and mitomycins. The vitamin-mitomycin conjugates are capable of selectively targeting a population of pathogenic cells in the host animal due to preferential expression of a receptor for the vitamin, accessible for vitamin binding, on the pathogenic cells. Acceptable vitamin moieties include niacin, pantothenic acid, folic acid, riboflavin, thiamine, biotin, vitamin $B_{12}$, and the lipid soluble vitamins A, D, E and K. These vitamins, and their receptor-binding analogs and derivatives, constitute the targeting entity that can be coupled with mitomycins by a cleavable linker to form the vitamin-mitomycin conjugates for use in accordance with the invention. Preferred vitamin moieties include folic acid, biotin, riboflavin, thiamine, vitamin $B_{12}$, and receptor-binding analogs and derivatives of these vitamin molecules, and other related vitamin receptor-binding molecules (see U.S. Pat. No. 5,688,488, incorporated herein by reference). Exemplary of a vitamin analog is a folate analog containing a glutamic acid residue in the D configuration (folic acid normally contains one glutamic acid in the L configuration linked to pteroic acid). The mitomycin compound can be any of the mitomycins or mitomycin-related compounds shown in Table 1 including mitomycin A, mitomycin B, mitomycin C, mitomycin D, mitomycin E, mitomycin F, mitomycin J, and porfiromycin, or analogs or derivatives thereof.

The binding site for the vitamin can include receptors for any vitamin molecule, or a derivative or analog thereof, capable of specifically binding to a receptor wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination of the pathogenic cells. In one embodiment, ligands that can be used in the conjugates of the present invention include those that bind to receptors expressed specifically on activated macrophages, such as the folate receptor, which binds folate or an analog or derivative thereof.

In accordance with the invention the vitamin-mitomycin conjugates are capable of high affinity binding to receptors on cancer cells or other pathogenic cells. The high affinity binding can be inherent to the vitamin moiety or the binding affinity can be enhanced by the use of a chemically modified vitamin (i.e., an analog or a derivative) or by the particular chemical linkage between the vitamin and the mitomycin compound that is present in the conjugate.

The linker can be any biocompatible cleavable linker, such as a linker susceptible to cleavage under the reducing conditions present in cells, an acid-labile linker, or an enzyme-labile linker. Typically, the linker comprises about 1 to about 30 carbon atoms, more typically about 2 to about 20 carbon atoms. Lower molecular weight linkers (i.e., those having an approximate molecular weight of about 30 to about 300) are typically employed.

Generally, any manner of forming a complex between the linker and the vitamin, or vitamin receptor binding derivative or analog, and between the linker and the mitomycin can be utilized in accordance with the present invention. The complex can be formed by direct conjugation of the cleavable linker with the vitamin and the mitomycin, for example, through hydrogen, ionic, or covalent bonds. Covalent bonding of the vitamin, or vitamin receptor binding derivative or analog, and the mitomycin with the linker can occur, for example, through the formation of amide, ester, disulfide, or imino bonds between acid, aldehyde, hydroxy, amino, sulfhydryl, or hydrazo groups. Also, in accordance with this invention the linker can comprise an indirect means for associating the vitamin with the mitomycin, such as by connection through intermediary linkers, spacer arms, or bridging molecules. Both direct and indirect means for association should not prevent the binding of the vitamin, or vitamin receptor binding derivative or analog, to the vitamin receptor on the cell membrane for operation of the method of the present invention.

The invention also provides a method of preparing a biologically active conjugate of the formula

B-L-X wherein B is a vitamin or a vitamin-receptor-binding analog or derivative thereof;

X comprises a mitomycin compound or an analog or derivative thereof;

and L is a divalent linker comprising a disulfide bond, said method comprising the steps of forming a thiosulfonate intermediate of the formula B-(L')$_n$SSO$_2$R or an intermediate of the formula X-(L')$_n$SSO$_2$R.

and reacting said thiosulfonate intermediate with a compound of the formula X-(L')$_{n'}$-SH or B-(L")$_{n'}$-SH, respectively, wherein L' and L" are, independently, divalent linkers through which the thiol group SH is covalently bonded to B and X, respectively;

n and n' are 1 or 0; and

R is alkyl, substituted alkyl, aryl, heteroaryl or substituted aryl or heteroaryl.

The nature of the linking groups L' and L" in the intermediates are not critical except that the linkers are preferably cleavable; nor is the nature of the group R on the thiosulfonate critical to the preparation of the vitamin conjugates. Precursors to such linking groups are typically selected to have either nucleophilic or electrophilic functional groups, or both, optionally in a protected form with a readily cleavable protecting group to facilitate their use in synthesis of the intermediate species. The linking group -L- in the conjugate, by virtue of the synthetic preparative procedure, can be represented as a composite of the intermediate linking group L' and L" by the formula -(L')$_n$-S—S-(L")$_{n'}$-. In the case of -L'-, the entity X-(L')$_n$-SH should retain cytotoxic activity.

The invention is also directed to pharmaceutical compositions comprising an amount of a vitamin-mitomycin conjugate effective to eliminate a population of pathogenic cells in a host animal when administered in one or more doses. The vitamin-mitomycin conjugate is preferably administered to the host animal parenterally, e.g., intradermally, subcutaneously, intramuscularly, intraperitoneally, intravenously, or intrathecally. Alternatively, the conjugate can be administered to the host animal by other medically useful processes, and any effective dose and suitable therapeutic dosage form, including prolonged release dosage forms, can be used. The method of the present invention can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the vitamin-mitomycin conjugate. In one preferred aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

At least one additional composition comprising a therapeutic factor can be administered to the host in combination or as an adjuvant to the above-detailed methodology, to enhance the vitamin-mitomycin mediated elimination of the population of pathogenic cells, or more than one additional therapeutic factor can be administered. The therapeutic factor(s) can be selected from a compound capable of stimulating an endogenous immune response, a chemotherapeutic agent, or another therapeutic factor capable of complementing the efficacy of the administered vitamin-mitomycin complex. The method of the invention can be performed by administering to the host, in addition to the above-described conjugates, compounds or compositions capable of stimulating an endogenous immune response including, but not limited to, cytokines or immune cell growth factors such as interleukins 1-18, stem cell factor, basic FGF, EGP, G-CSF, GM-CSF, FLK-2 ligand, HILDA, MIP-1α, TGF α, TGF β, M-CSF, IFN α, IFN β, IFN γ, soluble CD23, LIF, and combinations thereof.

Therapeutically effective combinations of these factors can be used. In one embodiment, for example, therapeutically effective amounts of IL-2, for example, in amounts ranging from about 5000 IU/dose/day to about 500,000 IU/dose/day in a multiple dose daily regimen, or, for example, in amounts ranging from about 7500 IU/dose/day to about 150,000 IU/dose/day in a multiple dose daily regimen, can be used along with the vitamin-mitomycin conjugates to eliminate pathogenic cells in a host animal harboring such a population of cells. Alternatively, IL-2 can be used in combination with IFN-α where IL-2 can be used, for example, in amounts ranging from 0.1 MIU/m$^2$/dose/day to about 15 MIU/m$^2$/dose/day in a multiple dose daily regimen, and IFN-α, for example, can be used in amounts ranging from about 0.1 MIU/m$^2$/dose/day to about 7.5 MIU/m$^2$/dose/day in a multiple dose daily regimen, along with the conjugates to eliminate or neutralize pathogenic cells in a host animal harboring the pathogenic cells (MIU=million international units; m$^2$=approximate body surface area of an average human). In another embodiment IL-12 and IFN-α are used in therapeutically effective amounts, and in yet another embodiment OL-15 and IFN-α are used in therapeutically effective amounts. In an alternate embodiment IL-2, IFN-α or IFN-γ, and GM-CSF are used in combination. The invention also contemplates the use of any other effective combination of cytokines including combinations of other interleukins and interferons and colony stimulating factors.

Chemotherapeutic agents, which are cytotoxic themselves, can work to enhance tumor permeability, can inhibit tumor growth or tumor cell proliferation, and the like, are also suitable for use in the method of the invention in combination with vitamin-mitomycin conjugates. Such chemotherapeutic agents include adrenocorticoids, alkylating agents, antiandrogens, antiestrogens, androgens, estrogens, antimetabolites such as cytosine arabinoside, purine analogs, pyrimidine analogs, and methotrexate, actinomycin D, gemcitabine, busulfan, carboplatin, chlorambucil, cisplatin and other platinum compounds, trimethoprim, dicloxacillin, daunorubicin, doxorubicin, epirubicin, mitoxantrone, topotecan, etoposide, tamoxiphen, TAXOL® (i.e., paclitaxel), cyclophosphamide, cyclosporin, plant alkaloids, prednisone, hydroxyurea, teniposide, bleomycin, digoxin, nitrogen mustards, nitrosureas, vincristine, vinblastine, mitomycin C, inflammatory and proinflammatory agents, and any other art-recognized chemotherapeutic agent.

The additional therapeutic factor can be administered to the host animal prior to, after, or at the same time as the vitamin-mitomycin conjugate and the therapeutic factor can be administered as part of the same composition containing the conjugate or as part of a different composition than the vitamin-mitomycin conjugate. Any such therapeutic composition containing the therapeutic factor at a therapeutically effective dose can be used in the present invention including compositions containing multiple therapeutic factors.

In one embodiment, the additional therapeutic factor is TAXOL® (i.e., paclitaxel; sold by Bristol Myers Squibb Company under the trademark TAXOL® and by Ivax Corporation under the trademark ONXOL™). In accordance with this invention, TAXOL®, ONXOL™, any other generic form of TAXOL®, or any related compound can be used in combination with the vitamin-mitomycin conjugates. TAXOL®, generic forms of TAXOL®, or related compounds can be administered, for example, to patients at doses of about 10 to about 500 mg/square meter, about 50 to about 400 mg/square meter, about 100 to about 300 mg/square meter, or about 100 to about 200 mg/square meter, but any effective dose in combination with the vitamin-mitomycin conjugates can be used.

Additionally, any effective regimen for administering TAXOL®, generic forms of TAXOL®, or a related compound can be used. For example, TAXOL® or generic or related compounds can be administered over 3 hours once every 3 weeks for a total of 18 weeks, but any other effective regimen is contemplated in accordance with this invention. TAXOL® or generic or related compounds can be administered by any effective route such as orally or parenterally, e.g., intradermally, subcutaneously, intramuscularly, intraperitoneally, intravenously, or intrathecally.

More than one type of drug delivery conjugate can be used. For example, the host animal can be treated with conjugates with different vitamins (e.g., folate-mitomycin conjugates and vitamin $B_{12}$-mitomycin conjugates) in a co-dosing protocol. In other embodiments, the host animal can be treated with conjugates comprising various vitamins linked to various mitomycins. For example, the host animal could be treated with a folate-mitomycin C and a folate-mitomycin A conjugate, or with a folate-mitomycin C conjugate and a vitamin $B_{12}$-mitomycin A conjugate. Furthermore, drug delivery conjugates with the same or different vitamins and the same or different mitomycins comprising multiple vitamins and multiple mitomycins as part of the same drug delivery conjugate could be used.

The unitary daily dosage of the vitamin-mitomycin conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. An effective dose can range from about 1 ng/kg to about 1 mg/kg, more preferably from about 1 µg/kg to about 500 µg/kg, and most preferably from about 1 µg/kg to about 100 µg/kg.

Any effective regimen for administering the vitamin-mitomycin conjugate can be used. For example, the vitamin-mitomycin conjugate can be administered as single doses, or it can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and within the scope of this invention. In one embodiment of the invention the host is treated with multiple injections of the vitamin-mitomycin conjugate to eliminate the population of pathogenic cells. In one embodiment, the host is injected multiple times (preferably about 2 up to about 50 times) with the vitamin-mitomycin conjugate, for example, at 12-72 hour intervals or at 48-72 hour intervals. Additional injections of the vitamin-mitomycin conjugate can be administered to the patient at an interval of days or months after the initial injections(s) and the additional injections prevent recurrence of the disease state caused by the pathogenic cells. Any additional therapeutic factor, such as a chemotherapeutic agent (e.g., paclitaxel), can also be administered after initial injections to prevent recurrence of disease.

In one embodiment, ligands that can be used in the conjugates of the present invention include those that bind to receptors expressed specifically on activated macrophages, such as the folate receptor which binds folate, or an analog or derivative thereof. The folate-mitomycin conjugates can be used to kill or suppress the activity of activated macrophages that cause disease states in the host. Such macrophage targeting conjugates, when administered to a patient suffering from an activated macrophage-mediated disease state, work to concentrate and associate the conjugated mitomycin in the population of activated macrophages to kill the activated macrophages or suppress macrophage function. Elimination or deactivation of the activated macrophage population works to stop or reduce the activated macrophage-mediated pathogenesis characteristic of the disease state being treated. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Conjugate administration is typically continued until symptoms of the disease state are reduced or eliminated, and the conjugate can be administered in combination with any additional therapeutic factor, such as a chemotherapeutic agent (e.g., paclitaxel).

The conjugates administered in accordance with the methods of this invention are preferably administered parenterally to the animal or patient suffering from the disease state, for example, intradermally, subcutaneously, intramuscularly, intraperitoneally, or intravenously in combination with a pharmaceutically acceptable carrier. Alternatively, the conjugates can be administered to the animal or patient by other medically useful procedures and effective doses can be administered in standard or prolonged release dosage forms. The therapeutic method of the present invention can be used alone or in combination with other therapeutic methods recognized for treatment of macrophage mediated disease states.

EXAMPLE 1

Preparation of Compounds 5, 7, and 9

Figure 5:
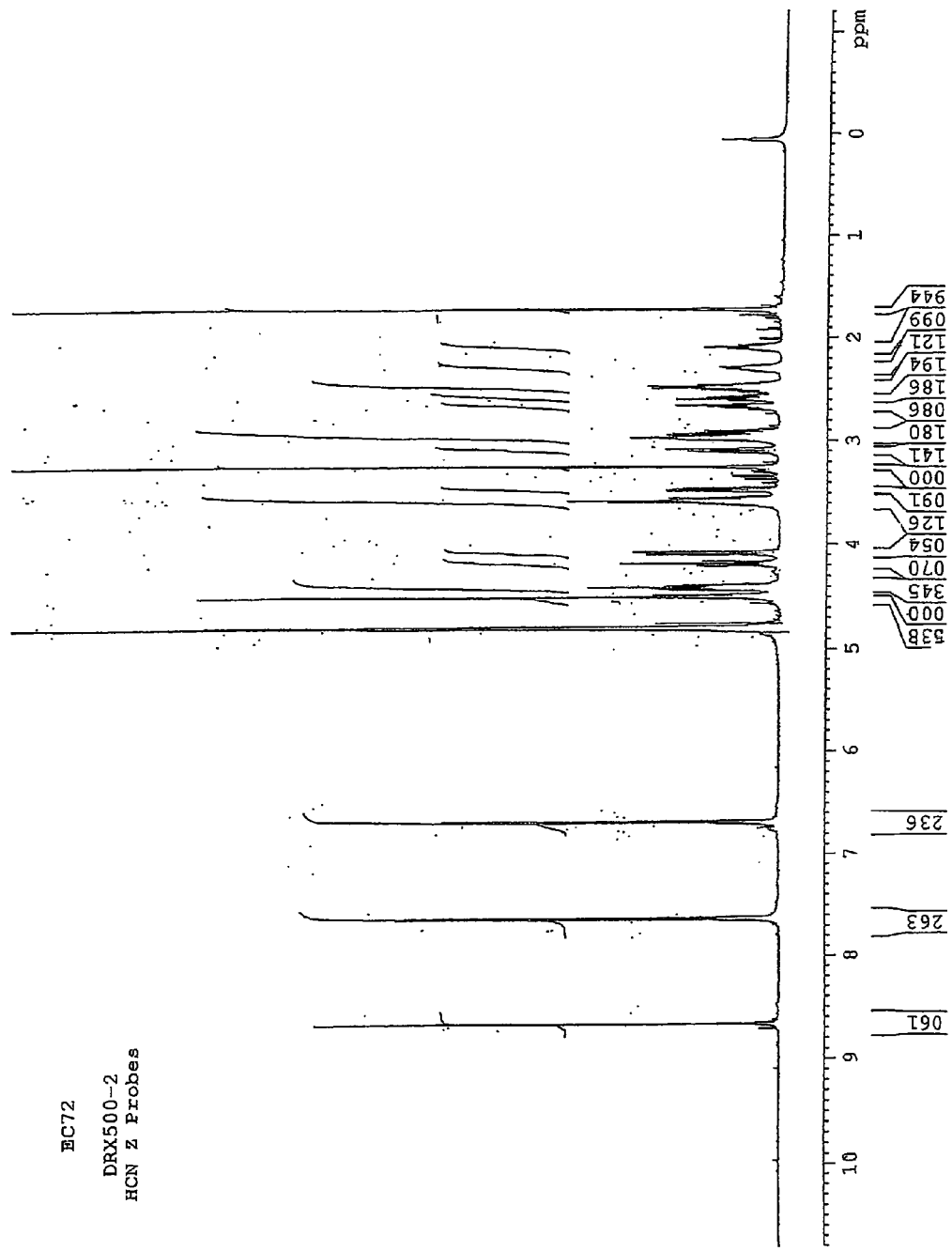
FIG. 5 shows 1D NMR of a pteroyl-Glu-Cys-S-mitomycin C conjugate (compound 5; see scheme 2), a Pte-Glu-Asp-Arg-Asp-Cys-S-mitomycin C—OH conjugate (compound 7; see scheme 2), and a Pte-Glu-Arg-Cys-S-mitomycin C-Ala-Gly-O conjugate (compound 9; see scheme 3).
Figure 6:
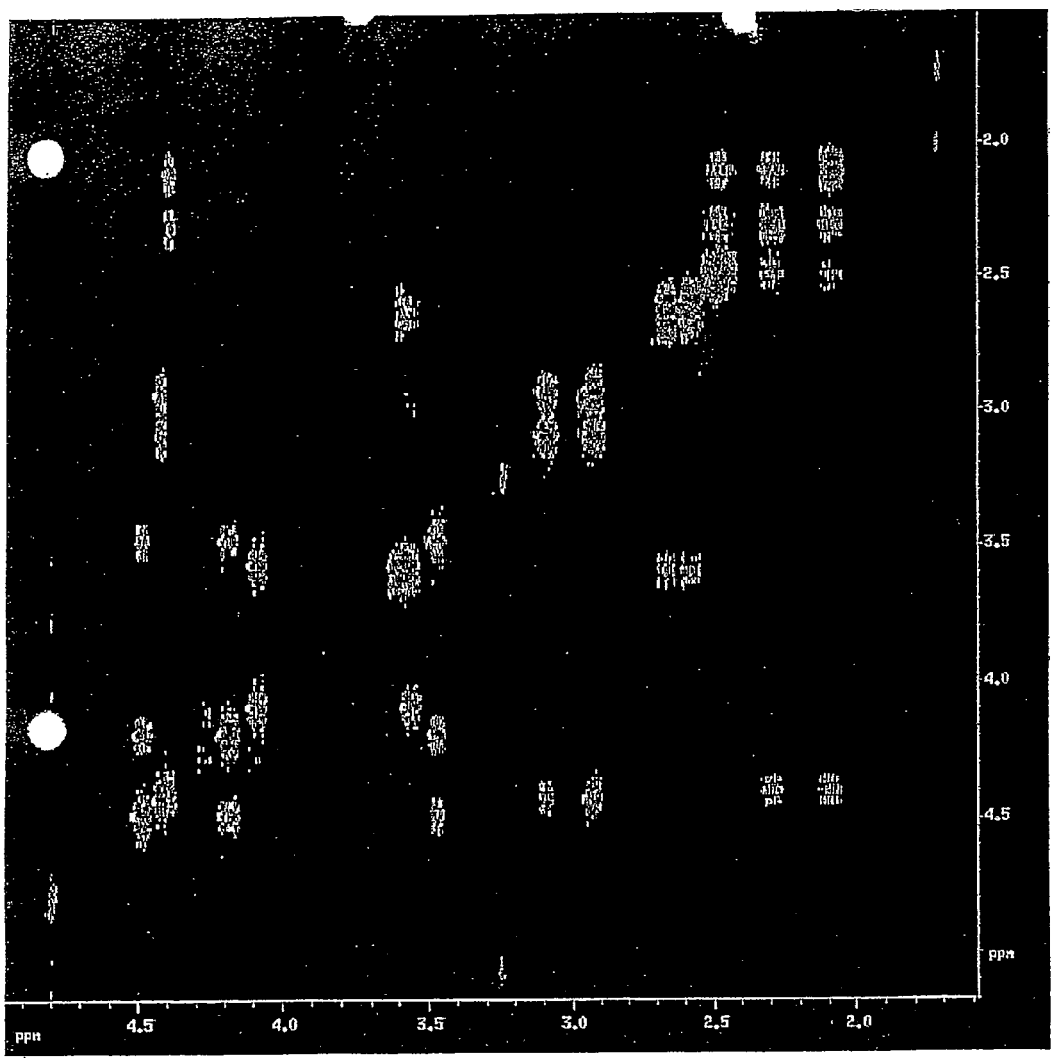
FIG. 6 shows 2D NMR of a pteroyl-Glu-Cys-S-mitomycin C conjugate (compound 5; see scheme 2), a Pte-Glu-Asp-Arg-Asp-Cys-S-mitomycin C—OH conjugate (compound 7; see scheme 2), and a Pte-Glu-Arg-Cys-S-mitomycin C-Ala-Gly-O conjugate (compound 9; see scheme 3).

Compounds 5, 7, and 9 (see schemes 2 and 3) were prepared as follows. First, compounds 1 and 2 (forty-five µmoles of each) were mixed with stirring under argon with 1 mL of anhydrous methanol. After stirring for 20 hours, both starting materials disappeared as determined by TLC (silica gel; $CHCl_3$/MeOH=9/1). To prepare compound 5, in a separate flask 1.0 mL of deionized water was added to forty-two µmoles of compound 4 and the solution was purged with argon. To this solution was added 0.1 N $NaHCO_3$ until the pH was adjusted to 7, and this solution was mixed with the first reaction solution described above (prepared by mixing compounds 1 and 2). The conjugation reaction was completed in 30 minutes. The methanol was evaporated i.vac. and the conjugate was purified on preparative HPLC (Prep Novapak HR C18 19×300 mM column; mobile phase (A)-1.0 mM phosphate buffer, pH=6; organic phase (13)-acetonitrile; conditions-gradient from 99% A and 1% B to 50% A and 50% B in 30 minutes, flow rate=15 mL/minute). Compounds 7 and 9 were prepared using the same protocol except that compounds 6 and 8, respectively, were used in the second solution in place of compound 4. Compounds 5, 7, and 9 were identified by 1D (FIG. 5) and 2D NMR (FIG. 6) and MS (ES).

EXAMPLE 2

Cytotoxicity of EC72 and Mitomycin C

A compound denominated as EC72 (see scheme 1) was evaluated using an in vitro cytotoxicity assay that predicts the ability of the drug to inhibit the growth of folate receptor-positive KB cells. This compound comprises a folate analog linked to mitomycin C prepared according to the protocol depicted in scheme 2. The KB cells were exposed for 15 minutes at 37° C. to the indicated concentrations of EC72, free mitomyicn C (drug #1), or to EC72 and at least a 100-fold excess of folic acid. The cells were then rinsed once with fresh culture medium and incubated in fresh culture medium for 72 hours at 37° C. Cell viability was assessed using a bromodeoxyuridine-based ELISA assay.

When compared directly, the cytotoxicity of EC72 was equal to that of free mitomycin C (see FIG. 1). The cytotoxicity of EC72 was blocked in the presence of excess free folic acid, indicating that the observed cell killing was mediated by folate binding to its receptor. Importantly, this result also suggests that normal tissues that express little to no folate receptor should not be affected by the EC72 conjugate.

EXAMPLE 3

Survival of Tumor-Bearing Mice Treated with EC72

The effectiveness of EC72 for promoting survival of tumor-bearing mice was evaluated in vivo using M109 tumor-bearing Balb/c mice. There were two goals of this study: i) to determine if daily intraperitoneal treatment with EC72 could prolong the lives of folate receptor-positive tumor-bearing mice beyond what mitomycin C could do when tested under an identical dosing regimen, and ii) to examine the pathological effects of EC72 treatment on normal tissues, including kidney tissue which is folate receptor-positive tissue. Although most normal tissues contain very low levels of folate receptor, the proximal tubules of the kidney express appreciable numbers of folate receptors. Thus, the in vivo evaluation of EC72 also enabled evaluation of the extent of kidney-specific damage caused by the systemic administration of folate-mitomycin conjugates.

Balb/c mice (5 mice/group) were given an intraperitoneal injection with $1\times10^6$ M109 cells. The mice were then given an intraperitoneal injection once daily with 1800 mmoles/kg of EC72 or mitomycin C (control mice were injected with PBS) beginning on day 5 after tumor cell innoculation (ILS=increased life span (i.e., median survival time)).

Figure 2:
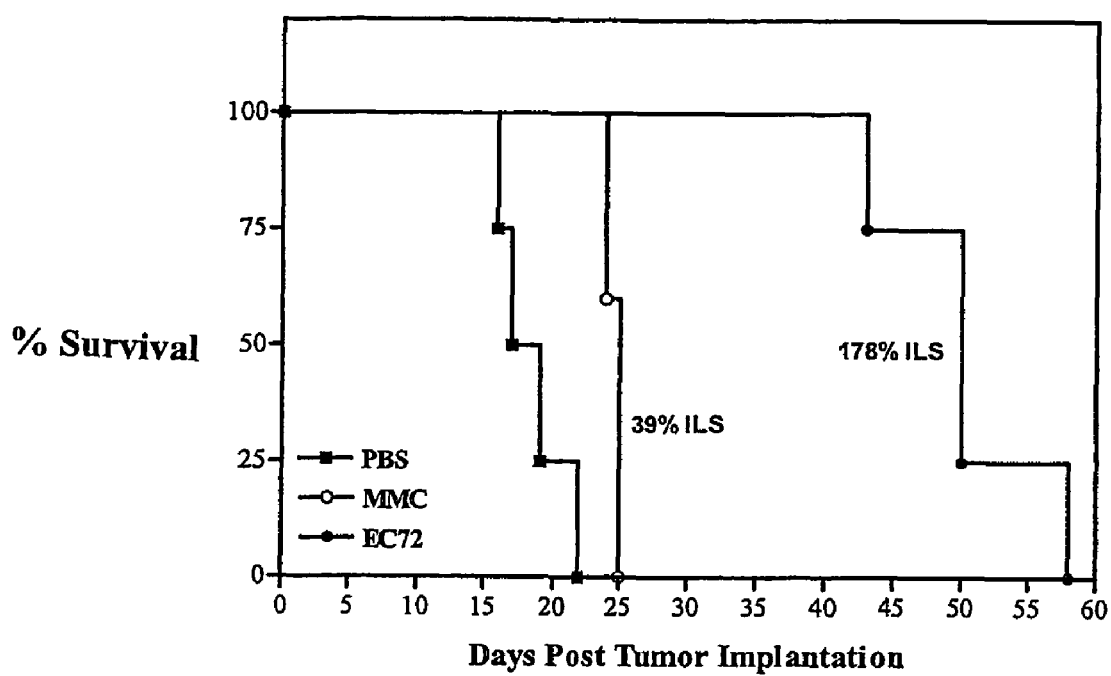
FIG. 2 shows the percentage survival of M109 tumor-bearing mice injected with PBS (control; closed squares), mitomycin C (open circles), or EC72 (closed circles).

As shown in FIG. 2, all control mice died by day 22 post tumor inoculation. While a 39% increase in lifespan (ILS) was observed for the animals treated with unmodified mitomycin C, the animals treated with EC72 had an average of a 178% increase in life span.

Figure 3:
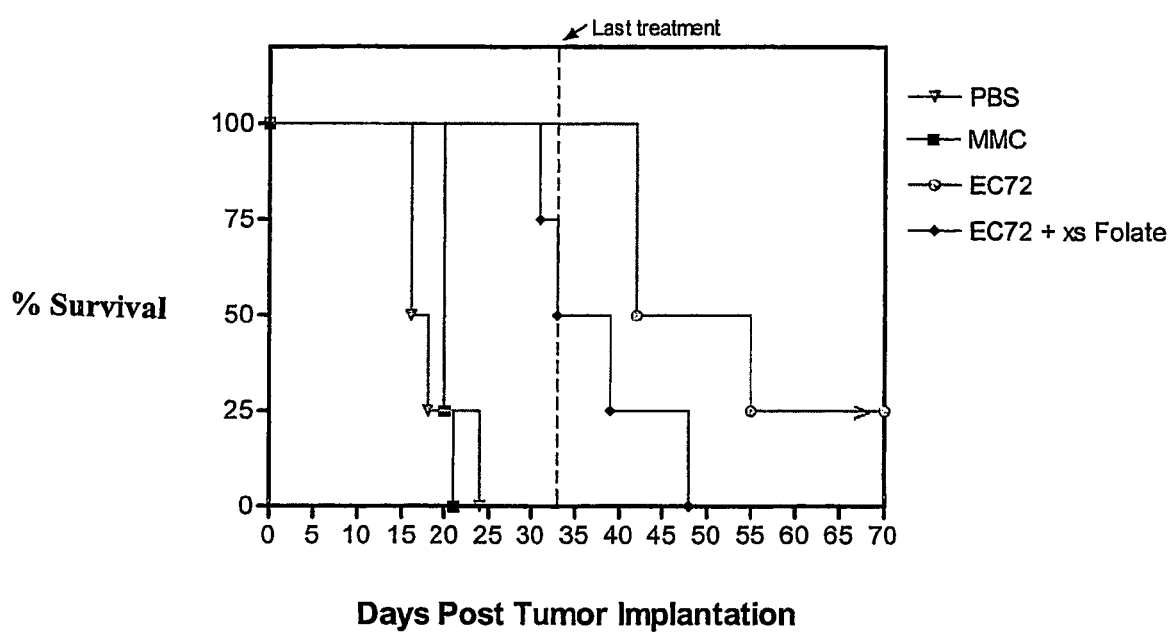
FIG. 3 shows the percentage survival of M109 tumor-bearing mice injected with PBS (control; closed triangles), mitomycin C (closed squares), EC72 (closed circles), or EC72 plus excess free folate (closed diamonds).

The same experiment (except that 30 daily injections with EC72 or mitomycin C were given) was repeated to confirm the observed EC72-mediated anti-tumor activity, and to confirm whether the effect of EC72 was mediated by folate binding to its receptor. Thus, a group of animals were given intraperitoneal injections of EC72 plus a 10-fold excess of free folic acid. As shown in FIG. 3, the group of animals treated with EC72 showed the greatest increased life span (i.e., median survival time; 185% over those of the PBS control group), while the animals in the mitomycin C group showed only an approximate 25% increase. Furthermore, 1 of 4 EC72-treated animals emerged tumor-free by day 70 post tumor cell inoculation. The anti-tumor effect of the EC72 conjugate was significantly reduced (112% increase in median survival time) by the coinjection of a moderate excess of folic acid, and all mice in this group eventually died from the tumor burden.

Major organs were also collected in both the EC72 and mitomycin C-treated animals (following euthanasia), and they were sent to an independent pathologist for examination. As described in Table 2 below, the mitomycin C-treated animals suffered from extensive myelosuppression, which is a characteristic side effect of mitomycin C therapy. In fact, all of the animals in this group died from apparent mitomycin C-related side effects. Surprisingly, animals treated with EC72 displayed no evidence of myelosuppression or kidney damage (i.e., the spleen, femur bone marrow and kidneys all appeared normal to the experienced pathologist). Interestingly, examination of blood collected from EC72 treated animals indicated normal blood-urea-nitrogen and creatine levels following 30 consecutive daily injections with EC72. Thus, folate-mitomycin C conjugates appear to be effective chemotherapeutic agents that do not cause unwanted injury to normal tissues, including the folate receptor-positive kidneys.

TABLE 2

| Test Article | Dose | Schedule/Route | Duration | Pathological Findings |
|---|---|---|---|---|
| Drug#1 | 1800 nmol/kg | q1d, i.p. | 21 days | Bone (femur) was completely depleted of marrow cells<br>Abnormal spleen: loss of all spleen-derived marrow tissue<br>Liver, kidney, heart, brain, lung, muscle and intestine visually appeared normal<br>No evidence of neoplasia in major organs |
| EC72 | 1800 nmol/kg | q1d, i.p. | 44 days | Bone marrow (femur) was normal<br>Spleen appeared normal<br>Kidney appeared normal<br>Occasional neoplasia found in liver, lung and intestine; no evidence of hemorrhage or degeneration<br>Animals died from tumor burden |

EXAMPLE 4

Survival of Tumor-Bearing Mice Injected Intravenously with EC72

The anti-tumor activity of EC72 when administered intravenously (i.v.) to tumor-bearing animals, was evaluated in Balb/c mice bearing subcutaneous M109 tumors. Thus, a protocol similar to that described in Example 3 was followed except that the compounds were administered i.v. (described below) and the tumors were subcutaneous. Four days post tumor inoculation in the subcutis of the right axilla, mice were injected i.v. qd×5 for six weeks with 1800 nmoles/kg of EC72.

Figure 4:
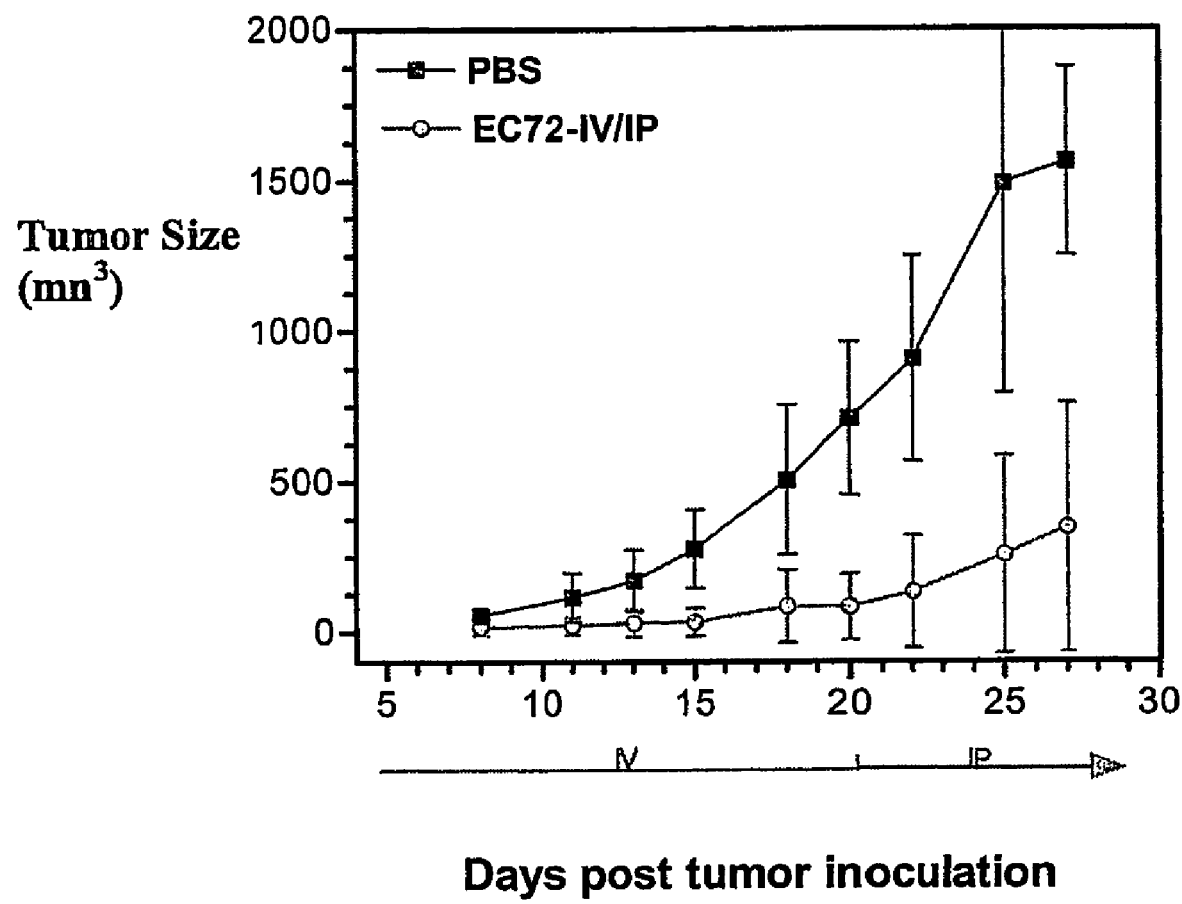
FIG. 4 shows tumor size in mice implanted with M109 cells to form subcutaneous tumors and treated with PBS (closed squares) or EC72 (closed circles).

Tumor growth was determined at 2-day intervals in each treatment group until the tumors grew to at least 1500 mm3. The tail veins became excessively bruised and inaccessible after 12 i.v. injections so dosing was continued i.p. following the same qd×5 schedule. As shown in FIG. 4, EC72 treatment was effective in delaying the growth of the M109 tumor. Interestingly, the tumors did begin to increase their growth rate shortly after the switch was made to i.p. dosing. Thus, EC72 may not have reached the distal subcutaneous tumor efficiently following i.p. administration of EC72, a limitation not encountered when EC72 was administered i.v. during the initial phase of the therapy.

EXAMPLE 5

Survival of Mice Bearing Solid Tumors Treated with EC72

The protocol described in Example 4 was followed except that mice were injected i.v. throughout the treatment period and were treated with EC72 for 4 weeks. Balb/c mice (n=5) were injected subcutaneously in the subcutis of the right axilla with $1\times10^6$ M109 cells and were treated qd×5 for 4 weeks with 1800 nmol/kg of EC72. EC72 was administered i.v. beginning on the designated day post tumor cell inoculation (PTI; see Table 3). Animal survival was monitored daily, and mice showing a complete response were those that were tumor-free at day 60 PTI.

In the subcutaneous tumor model, survival declined with the length in delay of EC72 administration. Thus, as summarized in Table 3, performance was maximal if treatment with EC72 began 1 day PTI, where 2 of 5 complete responses resulted and 3 of 5 animals had a 133% increase in lifespan (ILS; i.e., partial response). In contrast, delaying EC72 treatment until 12 days PTI resulted in only an 8% ILS with 0 of 5 complete responses. Also, median survival time (days) and % ILS decreased with an increasing delay in initiation of EC72 treatment.

TABLE 3

| Animals/cohort | n = 5 | n = 5 | n = 5 | n = 5 | n = 8 |
| --- | --- | --- | --- | --- | --- |
| Initiation of Treament | PTI 1 | PTI 3 | PTI 7 | PTI 12 | Untreated Controls |
| Median Survival (days) | 56 | 54 | 28 | 26 | 24 |
| % ILS | 133 | 125 | 17 | 8 | n/a |
| Partial Responses | 3 | 5 | 5 | 5 | n/a |
| Complete Responses | 2 | 0 | 0 | 0 | 0 |

EXAMPLE 6

Survival of Mice Bearing Solid Tumors Treated with EC72 and TAXOL®

The protocol described in Example 5 was followed except that animals were injected i.v. at the beginning of the treatment period and were injected i.p. later in the treatment period. To investigate whether EC72 and TAXOL® in combination might effectively increase survival of mice bearing solid tumors, subcutaneous M109 tumors were formed in Balb/c (n=5 for each treatment group) mice for 12 days (i.e., a time PTI when initiation of treatment with EC72 alone was ineffective (see Table 3)). The mice were then treated with TAXOL® (i.e., paclitaxel) with or without EC72, and both primary tumor volumes and survival of the animals were measured.

Twelve days PTI, the mice were treated with TAXOL® (20 mg/kg, i.v. on days 12, 15, 19, 22, and 26 PTI) with or without EC72 (1800 nmol/kg qd×5 for 4 weeks; i.v. on days 12, 15, 19, 22, and 26 PTI, and i.p. all remaining days). Tumor volumes were calculated using the equation $V=a\times b^2/2$, where "a" is the length of the tumor and "b" is the width expressed in millimeters. The tumors were measured using calipers.

Figure 7:
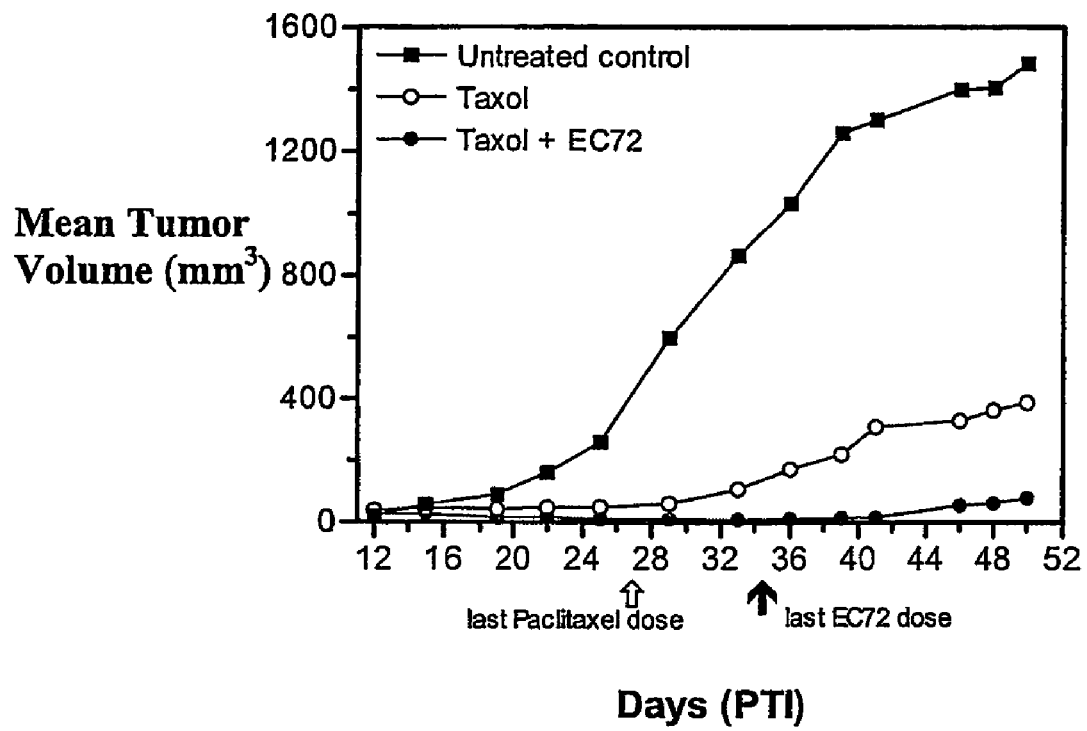
FIG. 7 shows tumor size in mice implanted with M109 cells to form subcutaneous tumors and treated with PBS (closed squares) or taxol (20 mg/kg; open circles), or taxol plus EC72 (closed circles).

As shown in FIG. 7, tumors in untreated control animals grew rapidly, and by day 50 PTI, they reached a size where euthanasia was required. Tumors in TAXOL®-treated animals failed to grow until day 29 PTI, after which they resumed growth. Although treatment with 20 mg/kg of TAXOL® alone resulted in a 1.3 log cell kill (LCK), the animals treated with TAXOL® alone appeared sick, experienced weight loss, and none of the 5 mice in the cohort were long term survivors. In contrast, tumors in mice treated with TAXOL® and EC72 in combination decreased in size during the dosing period, and this regimen resulted in a 1.8 LCK in 3 of the 5 mice in this cohort, and 2 of 5 mice were tumor-free at 90 days PTI. Furthermore, all of the mice treated with TAXOL® in combination with EC72 maintained their weight and appeared healthy throughout the dosing period. These results show that EC72 and TAXOL® act synergistically to prevent tumor growth because EC72 alone failed to produce an anti-tumor response in this subcutaneous tumor model when EC72 treatment was initiated 12 days PTI (see Table 3), and the response with EC72 and TAXOL®D in combination was much greater than with TAXOL® alone.

EXAMPLE 7

Survival of Mice Bearing Solid Tumors Treated with EC72 and TAXOL®

Figure 8:
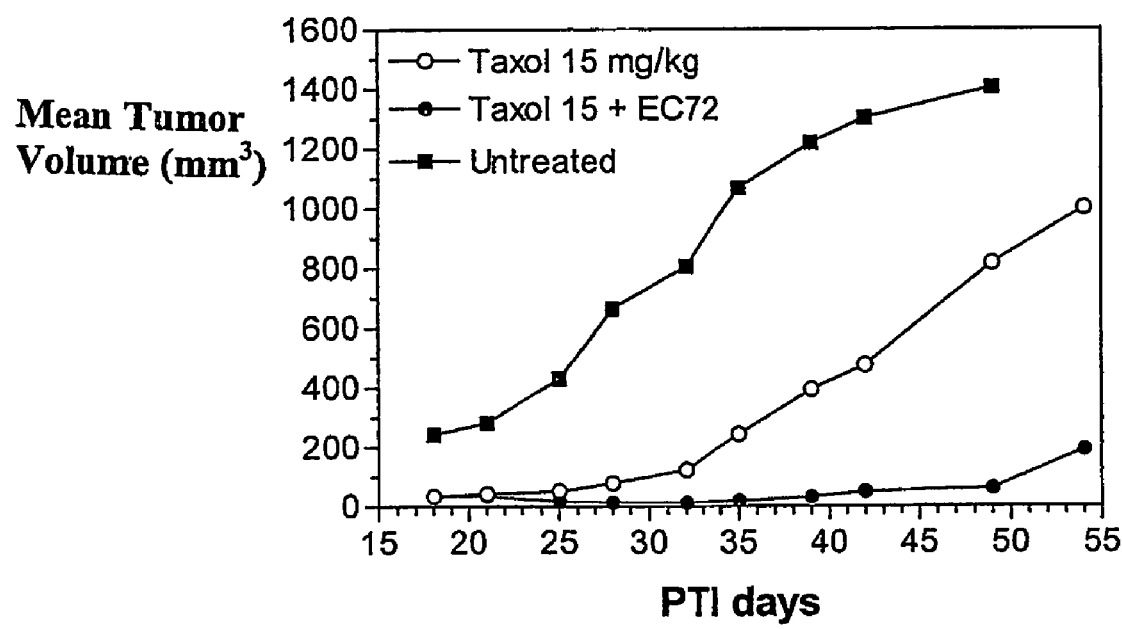
FIG. 8 shows tumor size in mice implanted with M109 cells to form subcutaneous tumors and treated with PBS (closed squares) or taxol (15 mg/kg; open circles), or taxol plus EC72 (closed circles).

The procedure described in Example 6 was followed except that TAXOL® was dosed at 15 mg/kg and 6 mice/cohort were tested. As shown in FIG. 8, tumors in untreated control animals grew at an exponential rate, and by day 50 PTI, they reached a size where euthanasia was required. In contrast, tumors in TAXOL®-treated mice failed to grow until day 21 PTI, after which they resumed apparent normal exponential growth. TAXOL® therapy resulted in a 0.6 LCK with a 135% increase in mean survival time in 4 of the 6 treated animals, and 2 of the 6 mice were complete responders (see Table 4 where CR=complete response, PR=partial response, and NR=no response). As in Example 6, strikingly better results were obtained with the TAXOL®-treated animals that were also treated with EC72. Thus, the combination of TAXOL® and EC72 produced a 1.5 LCK with a 185% increase in mean survival time in 2 of 6 mice, and, importantly, 4 of the 6 mice were complete responders (see FIG. 8 and Table 4). Taken together, these results and the results shown in FIG. 7 demonstrate that TAXOL® and EC72 act synergistically to inhibit tumor growth.

TABLE 4

| Taxol Dose (mg/kg) | EC72 Dose (nmol/kg) | Log Cell Kill (LCK) | Mean Survival Time (% T/C) | CR | PR | NR |
|---|---|---|---|---|---|---|
| 15 | 0 | 0.6 | 135 | 2 | 4 | 0 |
| 15 | 1800 | 1.5 | 187 | 4 | 2 | 0 |

The toxicity of each tested regimen was also monitored by measuring weight loss, blood chemistry, and tissue pathology. Animals treated with TAXOL® in combination with EC72 appeared healthy and did not lose weight throughout the dosing period. Also, the tissue pathology results from the mice treated with TAXOL® and EC72 confirmed that there was no major organ degeneration in these animals (Table 5).

TABLE 5

| | TAXOL ® 15 mg/kg, n = 6 mice | | TAXOL ® 15 mg/kg + EC72 n = 6 mice | |
|---|---|---|---|---|
| | Normal | Degeneration | Normal | Degeneration |
| Heart | 6 | | 5 | |
| Liver | 5 | 1(1) | 4 | 2(1) |
| Spleen | 6 | | 6 | |
| Kidney | 6 | | 5 | 1(2) |
| Bone | 6 | | 6 | |

"0.5" = Occasionally present,
"1" = Mild,
"2" = Moderate,
"3" = Marked

EXAMPLE 8

Relative Affinity Assay

Figure 9:
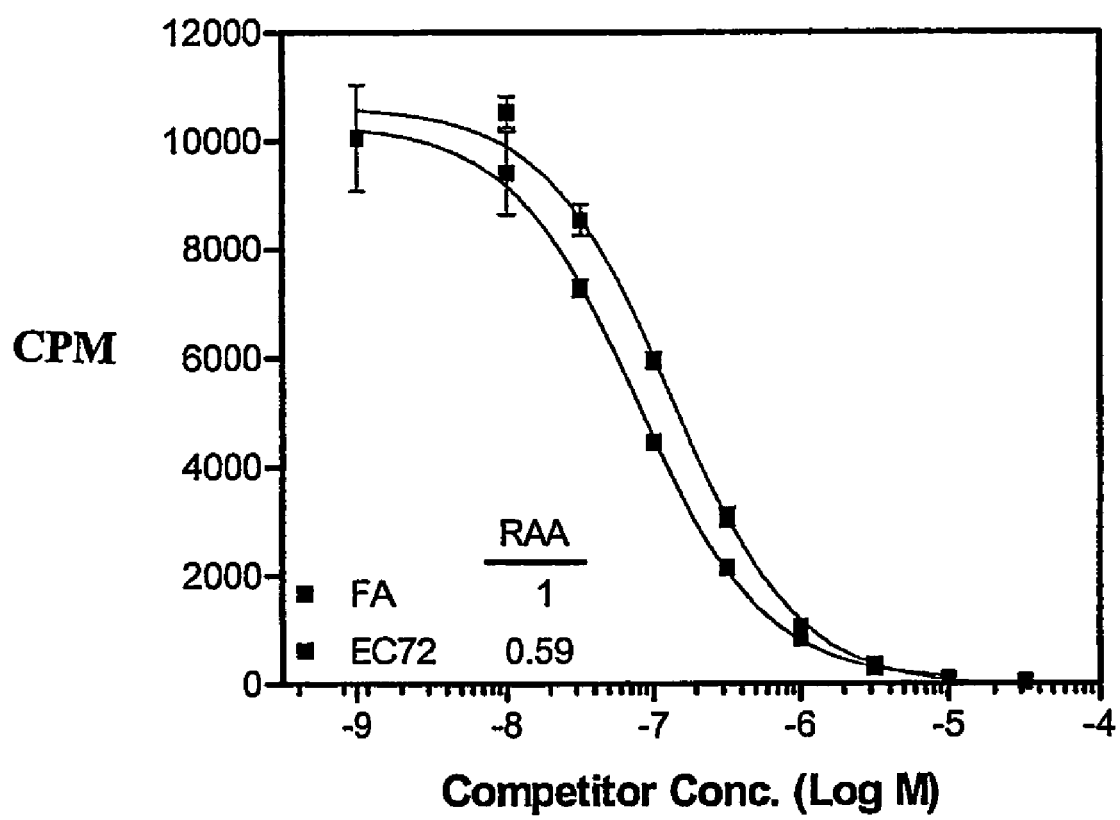
FIG. 9 shows $^3$H-folic acid binding to KB cells in the presence of increasing concentrations of free folic acid (lower curve) or EC72 (upper curve).

The affinity of EC72 for folate receptors (FRs) relative to folate was determined according to a previously described method (Westerhof, G. R., J. H. Schomagel, et al. (1995) Mol. Pharm. 48: 459-471) with slight modification. Briefly, FR-positive KB cells were gently trypsinized in 0.25% trypsin in phosphate-buffered saline (PBS) at room temperature for 3 minutes and then diluted in folate-free RPMI (FFRPMI) containing 10% heat-inactivated fetal calf serum (HIFCS). Following a 5 min 800×g spin and one PBS wash, the final cell pellet was suspended in FFRPMI 1640 (no serum). Cells were incubated for 15 min on ice with 100 nM $^3$H-folic acid in the absence and presence of increasing concentrations of EC72 or folate. Samples were centrifuged at 10,000×g for 5 min, and then the cell pellets were suspended in buffer, transferred to individual vials containing 5 mL of scintillation cocktail, and then counted for radioactivity. Negative control tubes contained only the $^3$H-folic acid in FFRPMI (no competitor). Positive control tubes contained a final concentration of 1 mM folic acid, and CPMs measured in these samples (representing non-specific binding of label) were subtracted from all samples. Notably, relative affinities were defined as the inverse molar ratio of compound required to displace 50% of $^3$H-folic acid bound to the FR on KB cells, and the relative affinity of folic acid for the FR was set to 1. As shown in FIG. 9, EC72 has a relative affinity of 0.59, indicating that this conjugate can effectively compete with folic acid (the native ligand) for binding to the folate receptor.

EXAMPLE 9

In Vitro Dose Response

Figure 10:
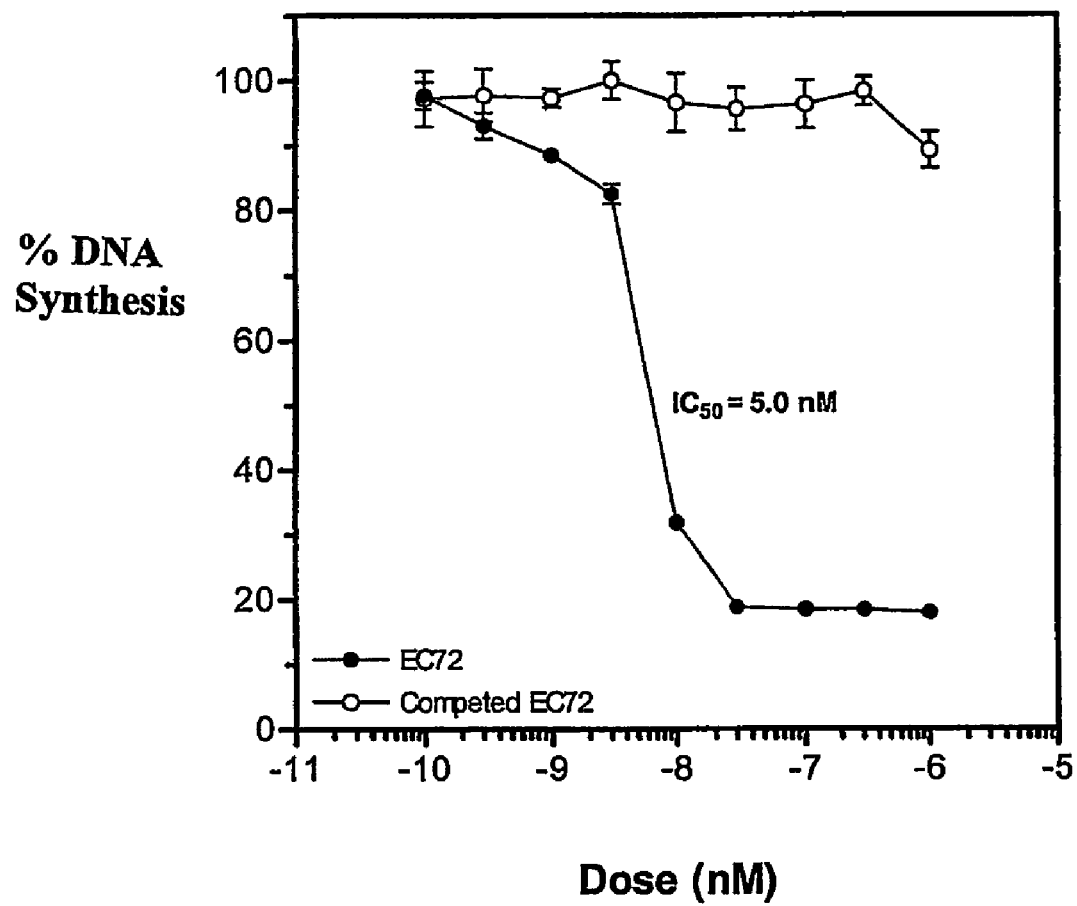
FIG. 10 shows the inhibition of KB cell DNA synthesis by increasing concentrations of EC72 (closed circles) or EC72 in the presence of 0.1 mM free folate (open circles).

KB cells were seeded in 12-well Falcon plates and allowed to form near-confluent monolayers overnight. Following one rinse with 1 mL of fresh FFRPMI/HIFCS, each well received 0.5 mL of FFRPMI/HIFCS containing increasing concentrations of EC72 in the presence of absence of 0.1 mM folic acid (competitor). Cells were incubated for 15 min at 37° C. and then rinsed four times with 0.5 mL of FFRPMI/HIFCS. 0.5 mL of fresh FFRPMI/HIFCS was then added to each well, and cells were chased for a total of 72 h at 37° C. Two hours before the end of the incubation, media was replaced in each well with 0.5 mL FFRPMI/HIFCS containing 5 µCi of $^3$H-thymidine. Monolayers were then washed 3 times with 0.5 mL of PBS and then precipitated with 1 ml of 10% cold trichloroacetic acid. The trichloroacetic acid solution was collected and discarded, and precipitated material was sequentially dissolved in 0.5 mL 0.25 N NaOH and 1% sodium dodecyl sulfate for 15 min at room temperature. Samples were then counted for radioactivity using a Packard gamma counter. Final tabulated values were expressed as a percentage of radioactivity incorporated into untreated cell samples. As shown in FIG. 10, EC72 displays high, dose-responsive activity against FR-positive KB cells (IC$_{50}$ 5 nM), and the activity is specific since an excess of free folic acid effectively blocked any DNA synthesis inhibition.

EXAMPLE 10

In Vivo Dose Response

Figure 11:
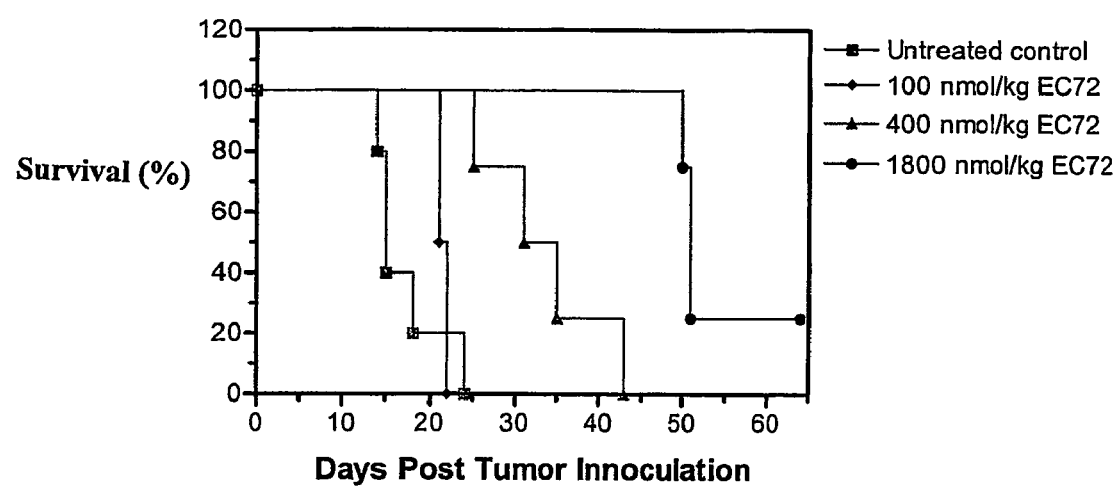
FIG. 11 shows the percentage survival of M109 tumor-bearing mice injected with PBS (control; closed squares) or increasing concentrations of EC72 (closed diamonds=100 nmol/kg of EC72, closed triangles=400 nmol/kg of EC72, and closed circles=1800 nmol/kg of EC72).

Six to seven week-old mice (female Balb/C strain) were obtained from Harlan, Inc., Indianapolis, Ind. The mice were maintained on Harlan's folate-free chow for a total of three weeks prior to the onset of and during this experiment. Folate receptor-positive M109 P$_0$ tumor cells (0.5×10$^6$ cells per animal) were inoculated in the upper peritoneal cavity 4 days prior to the onset of dosing. The formulations indicated in FIG. 11 were dosed intraperitoneally qd×30 starting on day 4 post tumor inoculation, and animal survival was monitored daily. EC72 displayed dose-dependent activity in M109 tumor-bearing mice. At the 1800 nmol/kg dose level of EC72 (saturable to folate receptors in vivo), a 240% increase in lifespan was observed with 1 of 4 animals showing a complete response.

EXAMPLE 11

In Vivo Activity on Folate Receptor-Negative Tumor

Figure 12:
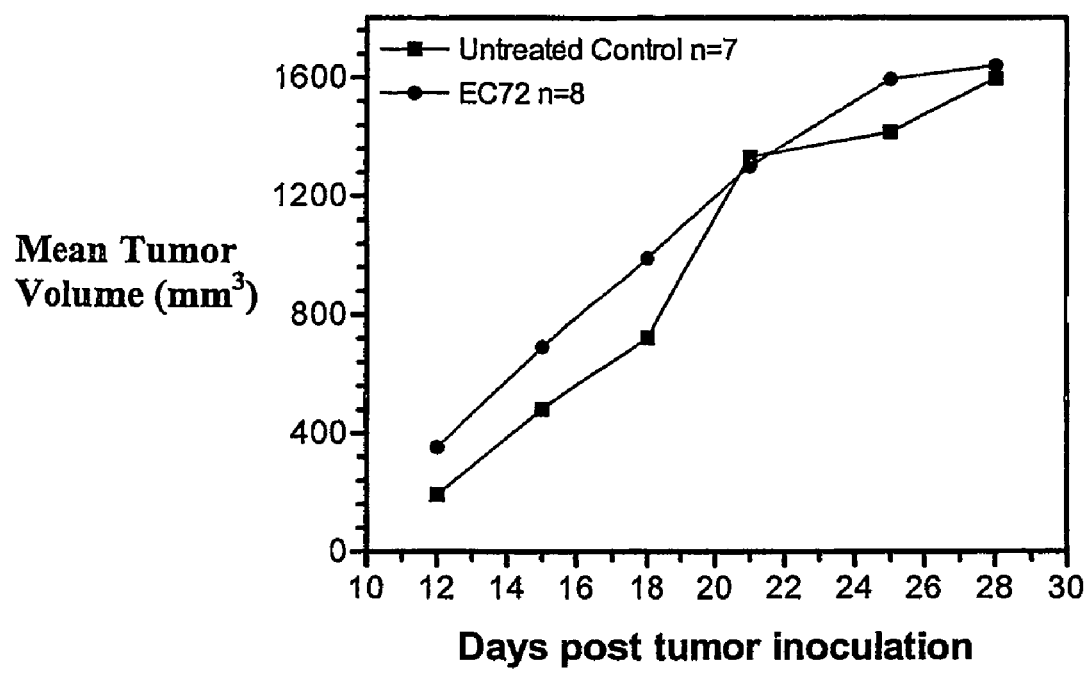
FIG. 12 shows tumor size in mice implanted with folate receptor-negative 4T-1 cells to form subcutaneous tumors and treatment with PBS (closed squares) or EC72 (closed circles).

Six to seven week-old mice (female Balb/C strain) were obtained from Harlan, Inc., Indianapolis, Ind. The mice were maintained on Harlan's folate-free chow for a total of three weeks prior to the onset of and during this experiment. Folate receptor-negative 4T-1 tumor cells (1×106 cells per animal) were inoculated in the subcutis of the right axilla. The formulations indicated in FIG. 12 were dosed intraperitoneally qd×30 starting on day 4 post tumor inoculation, and tumor volume as well as animal survival were monitored daily. EC72 had no activity against a subcutaneous folate-receptor-negative 4T-1 tumor.

The invention claimed is:

1. A conjugate of the general formula

B-L-X wherein the group B is folate, or an analog or a derivative thereof, that binds to a surface accessible folate receptor that is uniquely expressed, overexpressed, or preferentially expressed by a population of pathogenic cells;
wherein the group L comprises a cleavable linker and wherein the cleavable linker is a disulfide group; and
wherein the group X comprises a mitomycin compound, or an analog or a derivative thereof.

2. The conjugate of claim 1 wherein the linker is cleaved under reducing conditions.

3. The conjugate of claim 1 wherein the mitomycin is selected from the group consisting of mitomycin A, mitomycin B, mitomycin C, mitomycin D, mitomycin E, mitomycin F, and porfiromycin.

4. A method of selectively eliminating a population of pathogenic cells in a host animal harboring said population of cells wherein the members of said cell population have a surface accessible binding site for folate, or an analog or derivative thereof, said method comprising the steps of:
administering to said host a conjugate of the general formula

B-L-X wherein the group B is folate, or an analog or a derivative thereof, that binds to a surface accessible folate receptor that is uniquely expressed, overexpressed, or preferentially expressed by the population of pathogenic cells;
wherein the group L comprises a cleavable linker and wherein the cleavable linker is a disulfide group; and
wherein the group X comprises a mitomycin compound, or an analog or a derivative thereof; and
selectively eliminating said population of pathogenic cells.

5. The method of claim 4 wherein the linker is cleaved under reducing conditions.

6. The method of claim 4 wherein the mitomycin is selected from the group consisting of mitomycin A, mitomycin B, mitomycin C, mitomycin D, mitomycin E, mitomycin F, and porfiromycin.

7. The method of claim 4 wherein the population of pathogenic cells is a cancer cell population.

8. The method of claim 4 further comprising the step of administering to said host a therapeutic factor selected from the group consisting of a cell killing agent, a tumor penetration enhancer, a chemotherapeutic agent, a cytotoxic immune cell, and a compound capable of stimulating an endogenous immune response.

9. The method of claim 8 wherein the therapeutic factor is a chemotherapeutic agent.

10. The method of claim 9 wherein the chemotherapeutic agent is paclitaxel.

11. A pharmaceutical composition comprising a conjugate of the general formula

B-L-X wherein the group B is folate, or an analog or a derivative thereof, that binds to a surface accessible folate receptor that is uniquely expressed, overexpressed, or preferentially expressed by a population of pathogenic cells;
wherein the group L comprises a cleavable linker and wherein the cleavable linker is a disulfide group; and
wherein the group X comprises a mitomycin compound, or an analog or a derivative thereof; and
a pharmaceutically acceptable carrier therefor.

12. The composition of claim 11 wherein the linker is cleaved under reducing conditions.

13. The composition of claim 11 wherein the mitomycin is selected from the group consisting of mitomycin A, mitomycin B, mitomycin C, mitomycin D, mitomycin E, mitomycin F, and porfiromycin.

14. The composition of claim 11 further comprising a therapeutic factor selected from the group consisting of a cell killing agent, a tumor penetration enhancer, a chemotherapeutic agent, and a compound capable of stimulating an endogenous immune response.

15. The composition of claim 14 wherein the therapeutic factor is a chemotherapeutic agent.

16. The composition of claim 15 wherein the chemotherapeutic agent is paclitaxel.

17. A method of preparing a biologically active conjugate of the formula

B-L-X wherein B is folate or a folate-receptor-binding analog or derivative thereof;
X comprises a mitomycin compound or an analog or derivative thereof;
and L is a divalent linker comprising a disulfide bond, said method comprising the steps of forming a thiosulfonate intermediate of the formula B-(L")nSSO2R or an intermediate of the formula X-(L')nSSO2R
and reacting said thiosulfonate intermediate with a compound of the formula X-(L')n'-SH or B-(L")n'-SH, respectively, wherein L' and L" are, independently, divalent linkers through which the thiol group SH is covalently bonded to B and X, respectively;
n and n' are 1 or 0; and
R is alkyl, substituted alkyl, aryl, heteroaryl or substituted aryl or heteroaryl.

18. A conjugate comprising folate, or an analog or derivative thereof, linked by a cleavable linker to a mitomycin compound, or an analog or derivative thereof, wherein the cleavable linker is a disulfide group, wherein the folate binds to a surface accessible folate receptor that is uniquely expressed, overexpressed, or preferentially expressed by a population of pathogenic cells.

19. A method of selectively eliminating a population of pathogenic cells in a host animal harboring said population of cells wherein the members of said cell population have a surface accessible binding site for folate, or an analog or derivative thereof, said method comprising the steps of:
administering to said host a conjugate comprising folate, or an analog or derivative thereof, linked by a cleavable linker to a mitomycin compound, or an analog or derivative thereof, wherein the cleavable linker is a disulfide group, wherein the folate binds to a surface accessible folate receptor that is uniquely expressed, overexpressed, or preferentially expressed by a population of pathogenic cells; and
selectively eliminating said population of pathogenic cells.

* * * * *